US011591368B2

(12) United States Patent
Tsai Chang et al.

(10) Patent No.: US 11,591,368 B2
(45) Date of Patent: Feb. 28, 2023

(54) PEPTIDES FOR CANCER TREATMENT

(71) Applicants: CHUNG SHAN MEDICAL UNIVERSITY, Taichung (TW); TUNGHAI UNIVERSITY, Taichung (TW)

(72) Inventors: Jinghua Tsai Chang, Taichung (TW); Feng-Di Lung, Taichung (TW)

(73) Assignees: CHUNG SHAN MEDICAL UNIVERSITY, Taichung (TW); TUNGHAI UNIVERSITY, Taichung (TW)

( * ) Notice: Subject to any disclaimer, the term of this patent is extended or adjusted under 35 U.S.C. 154(b) by 0 days.

(21) Appl. No.: 16/609,119

(22) PCT Filed: Apr. 27, 2018

(86) PCT No.: PCT/US2018/029733
§ 371 (c)(1),
(2) Date: Oct. 28, 2019

(87) PCT Pub. No.: WO2018/200921
PCT Pub. Date: Nov. 1, 2018

(65) Prior Publication Data

US 2021/0032288 A1 Feb. 4, 2021

Related U.S. Application Data

(60) Provisional application No. 62/491,564, filed on Apr. 28, 2017.

(51) Int. Cl.
*C07K 7/08* (2006.01)
*A61P 35/00* (2006.01)
*A61K 38/00* (2006.01)
*A61K 45/06* (2006.01)

(52) U.S. Cl.
CPC ................ *C07K 7/08* (2013.01); *A61P 35/00* (2018.01); *A61K 38/00* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,008,058 | A | 12/1999 | Spatola et al. | |
| 2016/0168200 | A1 | 6/2016 | Weinschenk et al. | |
| 2018/0094284 | A1 * | 4/2018 | Jung | C12Y 114/99 |

OTHER PUBLICATIONS

UniProt Accession H0Y968. (Year: 2012).*
CAS RN 597592-24-0 (Year: 2003).*
CAS RN 665409-96-1 (Year: 2004).*
CAS RN 773716-63-5 (Year: 2004).*
CAS RN 2217695-83-3 (Year: 2018).*
GenBank AAH61648 (Year: 2004).*
GenBank CAL62764 (Year: 2015).*
UniProt O94813 (Year: 2003).*
Iwai H and Pluckthun A "Circular Beta-lactamase: stability enhancement by cyclizing the backbone" FEBS Lett. 459:166-172. (Year: 1999).*
Behrendt et al. "Advances in Fmoc solid-phase peptide synthesis" J. Peptide Sci. 22:4-27. (Year: 2016).*
Veronese F and Mero A "The Impact of PEGylation on Biological Therapies" Biodrugs 22:315-329. (Year: 2008).*
International Search Report and Written Opinion in International Patent Application No. PCT/US18/29733, dated Jul. 26, 2018, in 10 pages.
Extended European Search Report in EP Application No. 18791861.0, dated Dec. 8, 2020, in 8 pages.
Werbowetski-Ogilvie, T. E., et al. "Inhibition of medulloblastoma cell invasion by Slit." Oncogene 25.37 (2006): 5103-5112.
Dallol, Ashraf, et al. "Slit2, a human homologue of the *Drosophila* Slit2 gene, has tumor suppressor activity and is frequently inactivated in lung and breast cancers." Cancer Research 62.20 (2002): 5874-5880.
Suchting, Steven, et al. "Soluble Robo4 receptor inhibits in vivo angiogenesis and endothelial cell migration." The FASEB Journal 19.1 (2005): 121-123, published online Oct. 14, 2004.
Office Action and Search Report in Taiwan Counterpart Application No. 107114610, dated Oct. 14, 2019, in 7 pages; English translation provided.
UniProt Database H0Y968, Feb. 22, 2012, downloaded Oct. 14, 2019, 2 pages.

* cited by examiner

*Primary Examiner* — Sudhakar Katakam
*Assistant Examiner* — Zachary J Miknis
(74) *Attorney, Agent, or Firm* — Duane Morris LLP

(57) ABSTRACT

The invention pertains to cancer treatment or prevention field. Particularly, the invention provides peptide fragments from SLIT2 protein and their applications in inhibition of cancer growth, invasion and metastasis.

14 Claims, 25 Drawing Sheets
(14 of 25 Drawing Sheet(s) Filed in Color)

Specification includes a Sequence Listing.

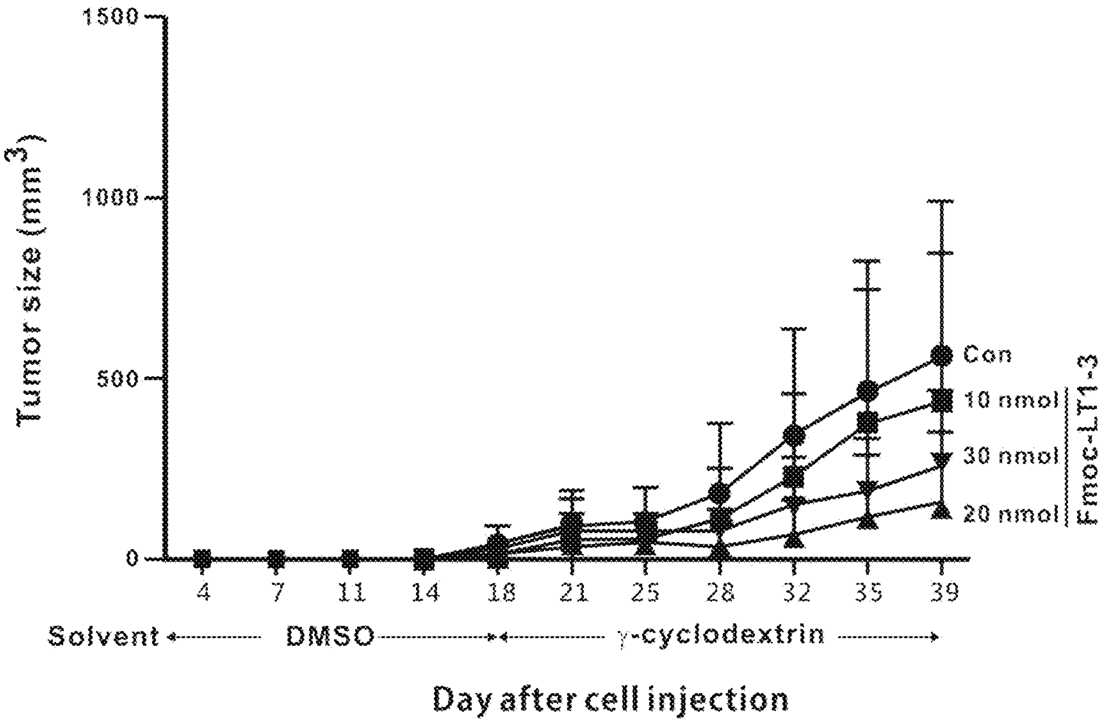
Fig. 7
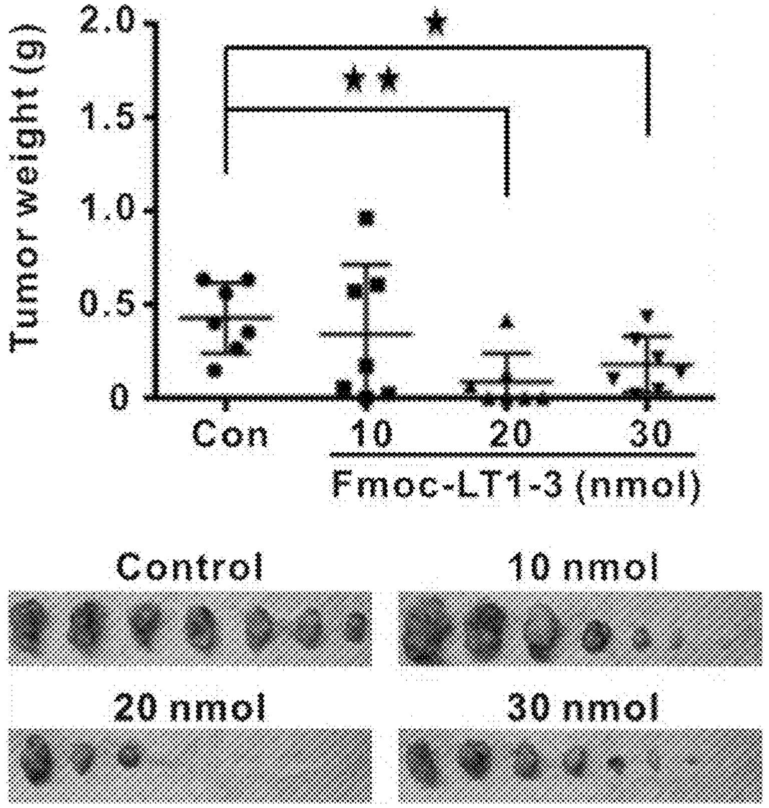
Fig, 8

PEPTIDES FOR CANCER TREATMENT

RELATED APPLICATIONS

This application is a U.S. National Phase 371 Application of International Application No. PCT/US2018/029733, filed Apr. 27, 2018, which claims the benefit of priority to U.S. Provisional Application No. 62/491,564, filed on Apr. 28, 2017, the contents of each of which are incorporated by reference herein in their entirtety.

FIELD OF THE INVENTION

The invention pertains to cancer treatment or prevention. Particularly, the invention provides peptide fragments from SLIT2 protein and their applications in inhibition of cancer growth, invasion and metastasis.

BACKGROUND OF THE INVENTION

Anti-cancer peptides have gained increased attention in recent years. However, most conventional anti-cancer drugs have low bioactivity and high toxicity. Therefore, there is a need to develop an anti-cancer bioactive peptide having high bioactivity and low toxicity.

SUMMARY OF THE INVENTION

The present disclosure provides a peptide comprising an amino acid sequence as described herein. Certain embodiments include the peptide comprising an amino acid sequence of FHIVELLA (SEQ ID NO:9) or FHAVELLA (SEQ ID NO:10). Other certain embodiments include cyclic peptide, pegylated peptide and fluorenylmethyloxycarbonyl-peptide as described herein.

The present disclosure provides a pharmaceutical composition, comprising a peptide of as described herein.

The present disclosure provides a method for inhibiting cancer growth, invasion and/or metastasis, comprising administering an effective amount of a peptide as described herein.

The present disclosure provides a method for preventing, treating, or ameliorating a cancer, comprising administering an effective amount of a peptide as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows the effect of Fmoc-LT1-3 on growth of tumor in xenograft model.

FIG. 8 shows size of tumor treated with different levels of LT1-3 peptide.

DETAILED DESCRIPTION OF THE INVENTION

Figure 1:
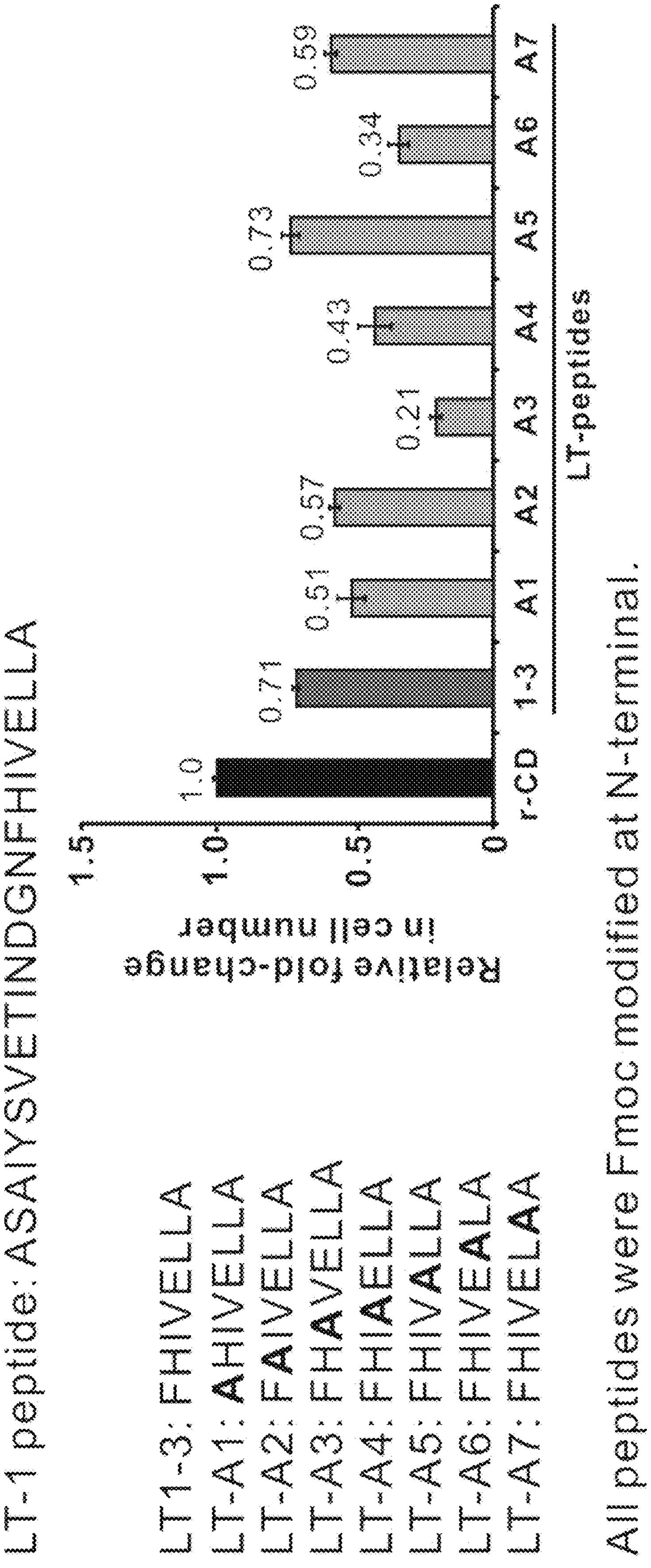
FIG. 1 shows the effect of alanine substitution of Fmoc-LT1-3 (LT1-3) on cell proliferation. The tested peptides are ASAIYSVETINDGNFHIVELLA (LT-1) (SEQ ID NO:2), FHIVELLA (LT1-3) (SEQ ID NO: 9), AHIVELLA (LT-A1) (SEQ ID NO:27), FAIVELLA (LT-A2) (SEQ ID NO:28), FHAVELLA (LT-A3) (SEQ ID NO:10), FHIAELLA (LT-A4) (SEQ ID NO:29), FHIVALLA (LT-A5) (SEQ ID NO:30), FHIVEALA (LT-A6) (SEQ ID NO:31), and FHIVELAA (LT-A7) (SEQ ID NO:32).

It will be understood that the various aspects and embodiments described herein are merely intended to provide illustration and do not serve to limit the scope of the claims.

Articles "a" and "an" are used herein to refer to one or to more than one (i.e. at least one) of the grammatical object of the article.

Abbreviations for amino acids are used throughout this disclosure and follow the standard nomenclature known in the art. For example, as would be understood by those of ordinary skill in the art, alanine is Ala or A; arginine is Arg or R; asparagine is Asn or N; aspartic acid is Asp or D; cysteine is Cys or C; glutamic acid is Glu or E; glutamine is Gln or Q; glycine is Gly or G; histidine is His or H; isoleucine is Ile or I; leucine is Leu or L; lysine is Lys or K; methionine is Met or M; phenylalanine is Phe or F; proline is Pro or P; serine is Ser or S; theonine is Thr or T; tryptophan is Trp or W; tyrosine is Tyr or Y; and valine is Val or V.

An amino acid having a hydrophobic side chain includes the non-limiting examples of alanine (A), isoleucine (I), leucine (L), methionine (M), phenylalanine (F), tryptophan (W), tyrosine (Y), and valine (V). An amino acid having a hydrophilic side chain includes the non-limiting examples of glycine (G), asparagine (N), glutamine (Q), serine (S), threonine (T), and cysteine (C). An amino acid having a basic side chain includes the non-limiting examples of histidine (H), lysine (K) and arginine (R). An amino acid having an acidic side chain includes the non-limiting examples of aspartic acid (D), and glutamic acid (E). An amino acid having a positively charged side chain, under typical physiological conditions, includes the non-limiting examples of arginine (R), histidine (H), and lysine (K). An amino acid having a negatively charged side chain, under typical physiological conditions, includes the non-limiting examples of aspartic acid (D) and glutamic acid (E). An amino acid having a polar uncharged side chain includes the non-limiting examples of serine (S), threonine (T), asparagine (N), and glutamine (Q).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

As used herein, "wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

As used herein, the term "amino acid" refers to natural amino acids, unnatural amino acids, and amino acid analogs, all in their D and L stereoisomers, unless otherwise indicated, if their structures allow such stereoisomeric forms.

As used herein, the term "peptide" or "oligopeptide" refers to organic compounds composed of amino acids, which may be arranged in either a linear chain (joined together by peptide bonds between the carboxyl and amino groups of adjacent amino acid residues) prior to cyclization, or in a cyclic form or in a constrained (e.g., "macrocycle") form.

As used herein, the term "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing pathology or to minimize the severity of the pathology, if developed.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, the term "therapeutically effective amount" or "efficacious amount" refers to the amount of a subject peptide that, when administered to a mammal or other subject for treating a disease, is sufficient to effect such treatment of the disease.

The present invention surprisingly found that fragments of SLIT2 protein have advantageous effects in inhibiting tumor growth and invasion. Particularly, the present invention found a fragment consisting of 91 amino acids from SLIT2 (ASAIYSVETINDGNFHIVELLALDQSLSLSVDGGNPKIITNLSKQSTLNFDSPLYVGGMP GKSNVASLRQAPGQNGTSFHGCIRNLYINSE) (SEQ ID NO:1), which has the effect in inhibiting both tumor growth and invasion. The present invention unexpected found that the following five overlapping peptide sequences in the SEQ ID NO:1 are effective in tumor growth and/or invasion.

```
                                  (SEQ ID NO: 2)
LT-1: ASAIYSVETINDGNFHIVELLA

                                  (SEQ ID NO: 3)
LT-2: FHIVELLALDQSLSLSVDGGNPKIIT

                                  (SEQ ID NO: 4)
LT-3: KIITNLSKQSTLNFDSPLYVGG

                                  (SEQ ID NO: 5)
LT-4: GGMPGKSNVASLRQAPGQNGTSF

                                  (SEQ ID NO: 6)
LT-5: LRQAPGQNGTSFHGCIRNLYINSE
```

LT-1 possesses an inhibitory effect on growth and invasion activity while LT-3, LT-4 and LT-5 have the inhibitory effect on cell invasion only. The N-terminal sequence of LT-2 contains the sequence of LT1-3 (SEQ ID NO:4), and thus it is highly possible that LT-2 has the inhibitory effect on growth and invasion activity.

Accordingly, the present disclosure provides a peptide comprising an amino acid sequence as shown in SEQ ID NO: 1, or a fragment thereof. In some embodiments, the fragment of the peptide comprises an amino acid sequence as shown in SEQ ID NO:2, 3, 4, 5 or 6.

The present invention also unexpectedly found that three fragments, a 10-amino acid fragment LT1-1 (ASAIYSVETI (SEQ ID NO:7), a 10-amino acid fragment LT1-2 (ETINDGNFHI (SEQ ID NO:8)) and an 8-amino acid fragment LT1-3 (FHIVELLA (SEQ ID NO:9), can be identified within the 22-amino acid fragment of LT-1 and that LT1-3 has a superior effect in inhibiting both tumor growth and invasion.

In one aspect, the invention provides a peptide comprising the following Formula I, $$X_1—X_2—X_3—X_4—X_5—X_6—X_7—X_8 \quad (I)$$

wherein $X_1$ is selected from an amino acid having a hydrophobic side chain; $X_2$ is selected from an amino acid having a basic side chain, an amino acid having an acidic side chain or an amino acid having a hydrophobic side chain; $X_3$ is selected from an amino acid having a hydrophobic side chain; $X_4$ is selected from an amino acid having a hydrophobic side chain; $X_5$ is selected from an amino acid having a basic side chain, an amino acid having an acidic side chain or an amino acid having a hydrophobic side chain; $X_6$ is selected from an amino acid having a hydrophobic side chain; $X_7$ is selected from an amino acid having a hydrophobic side chain or an amino acid having a hydrophilic side chain; and $X_8$ is selected from an amino acid having a hydrophobic side chain or an amino acid having a hydrophilic side chain; or a modified peptide or a salt thereof.

In some embodiments, $X_1$ is selected from F, A, Y and W; $X_2$ is selected from H, K, R, A and E; $X_3$ is selected from I or A; $X_4$ is selected from V and A; $X_5$ is selected from E, D, H, Orn, A and H; $X_6$ is selected from L and A; $X_7$ is selected from L and S and $X_8$ is selected from A and S; or a modified peptide or a salt thereof.

In some embodiments, the peptide comprises FHIVELLA (LT1-3) (SEQ ID NO:9), FHAVELLA (LT-A3) (SEQ ID NO:10), FKAVELLA (LT-K2) (SEQ ID NO:11), FRAVELLA (LT-R2) (SEQ ID NO:12), FHAVDLLA (LT-D5) (SEQ ID NO:13), FHAVHLLA (LT-H5) (SEQ ID NO:14), FHAVOLLA (LT-Orn5) (SEQ ID NO:15), AHAVELLA (LT-A13) (SEQ ID NO:16), FHAAELLA (LT-A34) (SEQ ID NO:17), FHAVEALA (LT-A36) (SEQ ID NO:18), FHAAEALA (LT-A346) (SEQ ID NO:19), FAIVALLA (LT-A25) (LT-A2) (SEQ ID NO:20), FEAVHLLA (LT-E2H5) (SEQ ID NO:21), YHAVELLA (LT-Y1) (SEQ ID NO:22), WHAVELLA (LT-W1) (SEQ ID NO:23), FHAVELSA (LT-S7) (SEQ ID NO:24), FHAVELLS (LT-S8) (SEQ ID NO:25), DGNFHIVELLA (LT-11AA) (SEQ ID NO:26), AHIVELLA (LT-A1) (SEQ ID NO:27), FAIVELLA (LT-A2) (SEQ ID NO:28), FHIAELLA (LT-A4) (SEQ ID NO:29), FHIVALLA (LT-A5) (SEQ ID NO:30), FHIVEALA (LT-A6) (SEQ ID NO:31), FHIVELAA (LT-A7) (SEQ ID NO:32), or a peptide comprising an amino acid sequence having one or several amino acid substitutions, deletions and/or additions in the amino acid sequence set forth in any of SEQ ID NOs: 9 to 32, and having an activity equal to or higher than that/those of the amino acid sequence set forth in any of SEQ ID NOs: 9-32; or a modified peptide or a salt thereof.

In further embodiments, the peptide of the present disclosure is FHAVELLA (SEQ ID NO:10); or a modified peptide or a salt thereof.

The peptide according to the present disclosure encompasses a peptide comprising an amino acid sequence having one or several amino acid substitutions, deletions and/or additions in the amino acid sequence set forth in Formula (I) (hereinafter also referred to as a "modified peptide"). It is a widely known fact for one of ordinary skill in the art that a peptide consisting of an amino acid sequence having one or several amino acid substitutions, deletions and/or additions in a certain amino acid sequence can maintain the biological activity of the original peptide.

In this context, in a case where one or several amino acids are substituted with other amino acids, the properties of amino acid side chains are preferably conserved before and after substitution. The properties of amino acid side chains include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy group-containing side chain (S, T, Y), amino acids having a sulfur atom-containing side chain (C, M), amino acids with a side chain having carboxylic acid or amide (D, N, E, Q), amino acids having a base-containing side chain (R, K, H), amino acids having an aromatic-containing side chain (H, F, Y, W) (each of the letters in parenthesis represents the one-letter notation for amino acids.

Further, the homology between a modified peptide and the original peptide is preferably 60% or more, more preferably 75% or more, even more preferably 85% or more, in particular preferably 95% or more, and most preferably 98% or more.

The peptides of the present disclosure can be modified to improve solubility or stability. In some embodiments, the modified peptide is a cyclic peptide, pegylated peptide or fluorenylmethyloxycarbonyl-peptide. For example, it is possible to arbitrarily add a set of polar residues or PEG (polyethylene glycol) to the peptide of the present disclosure to improve its solubility. The PEG can be added to the C terminal or N terminal of the peptide of the present disclosure. In one embodiment, the PEG is added to the N—or C— terminal of the peptide of the present disclosure. In some embodiments, the modified peptide is a PEG-peptide, wherein PEG binds to N terminal or C terminal of the peptide comprising an amino acid sequence selected from the group consisting of SEQ ID Nos:9 to 32. In an embodiment, the PEG-peptide is PEG-LT1-3 or PEG-LT-A3 (i.e. PEG binds to C terminal or N terminal of the peptide comprising an amino acid sequence selected from the group consisting of SEQ ID NO:9 or 10).

In one embodiment, a fluorenylmethyloxycarbonyl (Fmoc) is added to the peptide of the present disclosure to improve the stability. In some embodiments, the modified peptide is a Fmoc-peptide, wherein Fmoc binds to N terminal or C terminal of the peptide comprising an amino acid sequence selected from the group consisting of SEQ ID Nos:9 to 32. In an embodiment, the Fmoc-peptide is Fmoc-LT1-3 or Fmoc-LT-A3 (i.e. Fmoc binds to N terminal of the peptide comprising an amino acid sequence selected from the group consisting of SEQ ID NO:9 or 10).

The peptides can be produced using any means for making polypeptides known in the art, including, e.g., synthetic and recombinant methods. Because of their relatively small size, the peptides of the present disclosure may be directly synthesized in solution or on a solid support in accordance with conventional techniques. Various automatic synthesizers are commercially available and can be used in accordance with known protocols. For example, in some embodiments the peptides can be synthesized using synthetic chemistry techniques such as solid-phase synthesis, Merrifield-type solid-phase synthesis, t-Boc solid-phase synthesis, Fmoc solid-phase synthesis, BOP solid-phase synthesis, and solution-phase synthesis. In other embodiments, the peptides can be produced, for example, by expressing the peptide from a nucleic acid encoding the peptide in a cell or in a cell-free system according to recombinant techniques familiar to those of skill in the art. The peptides can incorporate any of the various modifications and protective groups known to those of skill in the art.

In one embodiment, the modified peptide of the present disclosure is in a cyclic form. In one embodiment, the modified peptide of the present disclosure is a cyclic that is formed by adding one or more hydrophilic amino acid, optionally one or more hydrophobic amino acid, at the N terminal of the peptide. In one embodiment, the cyclic peptide comprises two hydrophilic amino acids and one hydrophobic amino acid bonding to the N terminal of the peptide of the present disclosure.

In one embodiment, the peptide of the present disclosure is a cyclic form of the peptide of Formula I. In a further embodiment, the present disclosure provides a cyclic peptide having the following Formula II, $$X_{a1}—X_{a2}—X_{a3}—X_1—X_2—X_3—X_4—X_5—X_6—X_7—X_8 \quad (II)$$

wherein $X_{a1}$ bonds to $X_8$ as head to tail cyclization, and $X_{a1}$ is D; $X_{a2}$ is G; $X_{a3}$ is N; and $X_1$, $X_2$, $X_3$, $X_4$, $X_5$, $X_6$, $X_7$ and $X_8$ are each an amino acid as defined herein The peptide compound having a cyclic portion according to the present disclosure refers to a compound formed by the amide bonds or ester bonds of amino acids and/or amino acid analogs and has a cyclic portion resulting from covalent bond-mediated cyclization such as amide bond or carbon-carbon bond formation reaction.

The modified peptide compound having a cyclic portion according to the present disclosure is not particularly limited as long as the peptide is cyclized at the cyclic site. The posttranslational cyclization site is required to be a cyclization unit that forms functional groups providing for the compatibility of membrane permeability and metabolic stability (druglikeness). Any such cyclization method can be used without particular limitations. Examples of such methods include amide bond formation from carboxylic acid and amine and carbon-carbon bond formation using a transition metal as a catalyst, such as Suzuki reaction, Heck reaction and Sonogashira reaction. Thus, the peptide compound of the present disclosure contains at least one set of functional groups capable of such bond formation reaction.

The cyclic portion in the peptide compound of the present disclosure is preferably, for example, a cyclic portion formed by cyclization by chemical reaction after translational synthesis. Also, the cyclic portion is preferably a cyclic portion that can be formed even under reaction conditions not influencing nucleic acids such as RNA or DNA after translation.

In a further embodiment, the cyclic peptide of the present disclosure comprises an amino acid sequence of DGNFHIVELLA (SEQ ID NO:26), wherein D bonds to A as head to tail cyclization (Cyclic-LT-11AA).

The peptides of the present disclosure exhibit inhibition of both of tumor growth and invasion and thus can be used to treat a cancer.

In another aspect, the present disclosure provides a pharmaceutical composition, nanoparticle or liposome, comprising a peptide described herein. In one embodiment, the composition comprises a second anti-cancer agent. For example, the second anti-cancer agent includes, but is not limited to, erlotinib, afatinib, gefitinib, bevacizumab, ramucirumab, gefitinib, lapatinib, erlotinib, cisplatin, paclitaxel, methotrexate, cyclophosphamide, ifosfamide, chlorambucil, carmustine, carboplatin, vincristine, vinblastine, thiotepa, lomustine, semustine, 5-fluorouracil, corticosteroids, calcineurin inhibitors, NSAIDs, inhibitors of 5-lipoxygenase, and cytarabine.

Some embodiments relating to pharmaceutical compositions for therapeutic or prophylactic treatment provide for formulations specific for any of mucosal (oral, nasal, inhalation, rectal, vaginal, tracheal, etc.), parenteral, topical, or local administration. In some embodiments, the pharmaceutical compositions are suitably administered parenterally, e.g., intravenously, subcutaneously, intradermally, or intramuscularly. The pharmaceutical compositions of the present disclosure can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

In another aspect, the present disclosure provides a method for preventing, treating, or ameliorating a cancer, comprising administering an effective amount of a peptide described herein to a subject.

In another aspect, the present disclosure provides a method for inhibiting cancer growth, invasion and/or metastasis, comprising administering an effective amount of a peptide described herein to a subject.

In one embodiment, the method of the present disclosure further comprises a step of administering a second anti-cancer agent as described herein. In another embodiment, the peptide of the present disclosure and the second anti-cancer agent are administered concurrently or separately.

For example, the cancers treatable by the peptides, compositions and methods of the present disclosure include but are not limited to the group consisting of: neuroblastoma; bile duct cancer; lung cancer; non-small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, or stomach cancer and urothelial cancer.

Subjects to be treated by the methods described herein encompass mammalian subjects, including both human subjects and non-human (animal) subjects such as dogs, cats, rabbits, goats, horses, pigs, cattle, etc. The term "concurrently administered" as used herein means that two compounds are administered sufficiently close in time to achieve a combined (immunological) effect. Concurrent administration may thus be carried out by sequential administration or simultaneous administration (e.g., simultaneous administration in a common, or the same, carrier).

In some embodiments, the disclosed peptides and compositions may be administered by any suitable route of administration, including, but not limited to, injection (subcutaneous, intraperitoneal, intravenous, intrathecal, intramuscular, intracerebroventricular, and spinal injection), intranasal, oral, transdermal, parenteral, inhalation, nasopharyngeal or transmucosal absorption. Administration encompasses providing at least one peptide as described herein formulated as a pharmaceutical composition. Pharmaceutically acceptable carriers are well known to those of skill in the art. Determination of particular pharmaceutical formulations and therapeutically effective amounts and dosing regimen for a given treatment is within the ability of one of skill in the art taking into consideration, for example, patient age, weight, sex, ethnicity, organ (e.g., liver and kidney) function, the extent of desired treatment, the stage and severity of the disease and associated symptoms, and the tolerance of the patient for the treatment.

In embodiments relating to therapeutic applications, the administration can be performed on a subject already suffering from the disorder of interest. Those in the incubation phase or the acute phase of the disease can be treated by the methods described herein, either alone or in conjunction with other treatments, as suitably based on the particular disease/condition, patient, and combination. One of skill in the art will be able to determine when a combination treatment is or is not suitable. In therapeutic methods and uses, the peptides and composition described herein can be administered to a subject in an amount sufficient to treat, or at least partially arrest, symptoms and/or complications. An amount adequate to accomplish this is often referred to as "therapeutically effective dose." Amounts effective for this use will depend in part on the peptide, composition, the manner of administration, the stage and severity of the condition being treated, the age, weight, and general health of the patient, and the judgment of the prescribing physician.

Without further elaboration, it is believed that one skilled in the art can utilize the present disclosure to its fullest extent on the basis of the preceding description. The following examples are, therefore, to be construed as merely illustrative and not a limitation of the scope of the present disclosure in any way.

EXAMPLES

Example 1 Preparation of LT-peptides

Dimethyl sulfoxide (DMSO; >99.9%) and 7-cyclodextrin (7-CD; 2.5 mM in RPMI-1640 (serum free)) were used as solvents to dissolved LT-peptides. LT peptides were dissolved in DMSO or 7-CD to a final 2.5 mM concentration and vortexed for 30 min. The peptide solutions were further diluted to 1 mM, 0.5 mM, and 50 μM using RPMI medium. The LT1-3-PEG peptide can be dissolved in RPMI-1640 directly. The peptide solutions were observed under microscope to examine their solubility.

Example 2 Cell Proliferation Assay

The peptides described below were Fmoc modified and dissolved in DMSO and 7-CD and then used in cell proliferation assay. CL1-5 cells were cultured to 80% confluence in RPMI medium containing 10% FBS. After detachment, $3\times10^4$□cells were seeded onto 12-well plates. After 16 h of incubation, cells were either harvested before treatment (designated as 0 h), or treated with LT peptides for 24 h (designated 24 h), and viable cells were counted. Relative fold-change in cell number or percent increase in cell growth (%) was calculated by following formula:

$$(\text{Cell number}_{24h} - \text{Cell number}_{0h})/(\text{Cell number of control}_{24h} - \text{Cell number of control}_{0h}).$$

Figure 2:
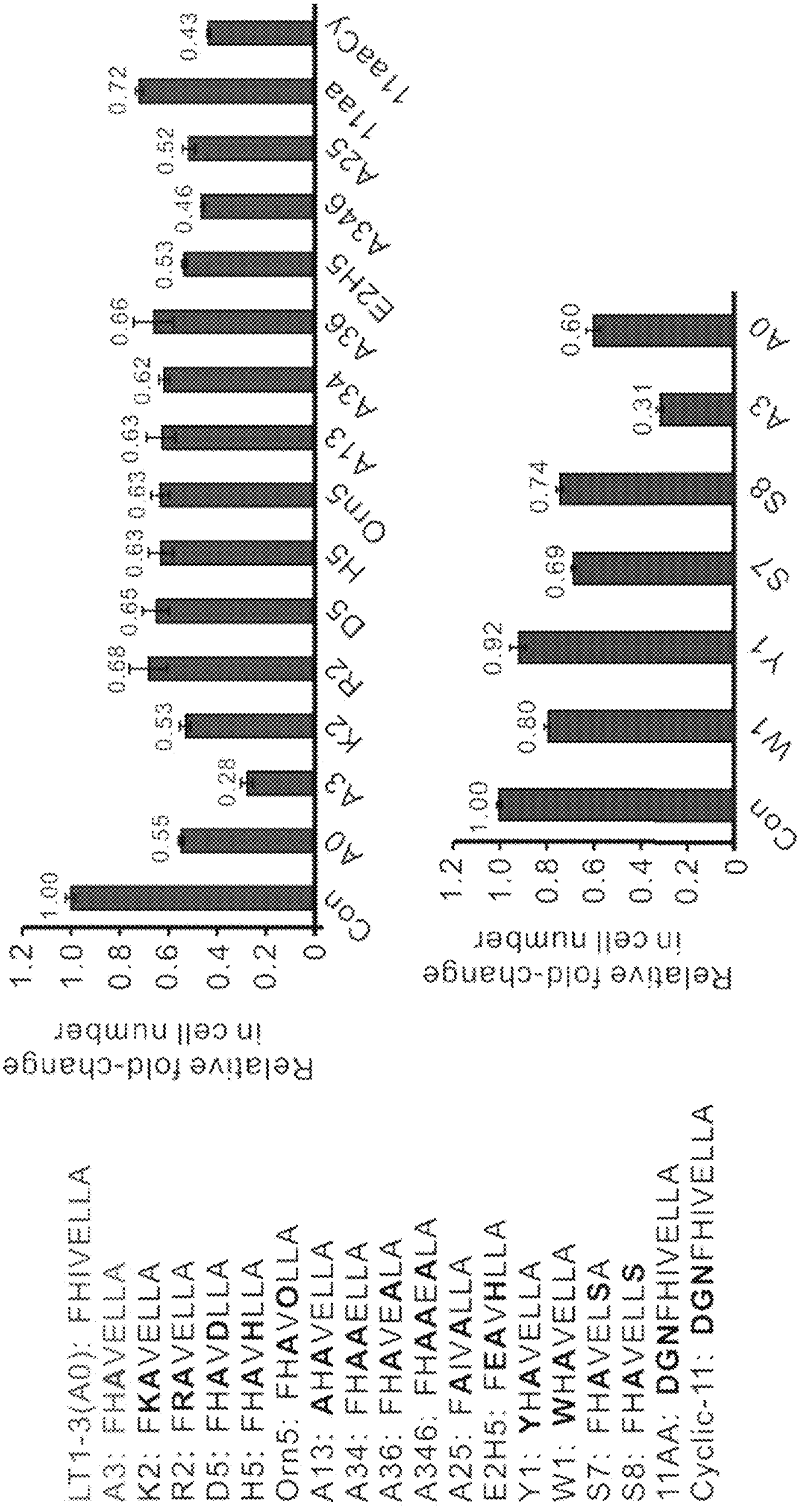
FIG. 2 shows the effect of base substitutions of Fmoc-LT-A3 (LT-A3) on cell proliferation. The tested peptides are FHIVELLA (LT1-3) (SEQ ID NO: 9), FHAVELLA (LT-A3) (SEQ ID NO:10), FKAVELLA (LT-K2) (SEQ ID NO:11), FRAVELLA (LT-R2) (SEQ ID NO:12), FHAVDLLA (LT-D5) (SEQ ID NO:13), FHAVHLLA (LT-H5) (SEQ ID NO:14), FHAVOrnLLA (LT-Orn5) (SEQ ID NO:15), AHAVELLA (LT-A13) (SEQ ID NO:16), FHAAELLA (LT-A34) (SEQ ID NO:17), FHAVEALA (LT-A36) (SEQ ID NO:18), FHAAEALA (LT-A346) (SEQ ID NO:19), FAIVALLA (LT-A25) (SEQ ID NO:20), FEAVHLLA (LT-E2H5) (SEQ ID NO:21), YHAVELLA (LT-Y1) (SEQ ID NO:22), WHAVELLA (LT-W1) (SEQ ID NO:23), FHAVELSA (LT-S7) (SEQ ID NO:24), FHAVELLS (LT-S8) (SEQ ID NO:25), DGNFHIVELLA (LT-11AA) (SEQ ID NO:26), and cyclic DGNFHIVELLA (LT-Cyclic-11) (SEQ ID NO:26).
Figure 3:
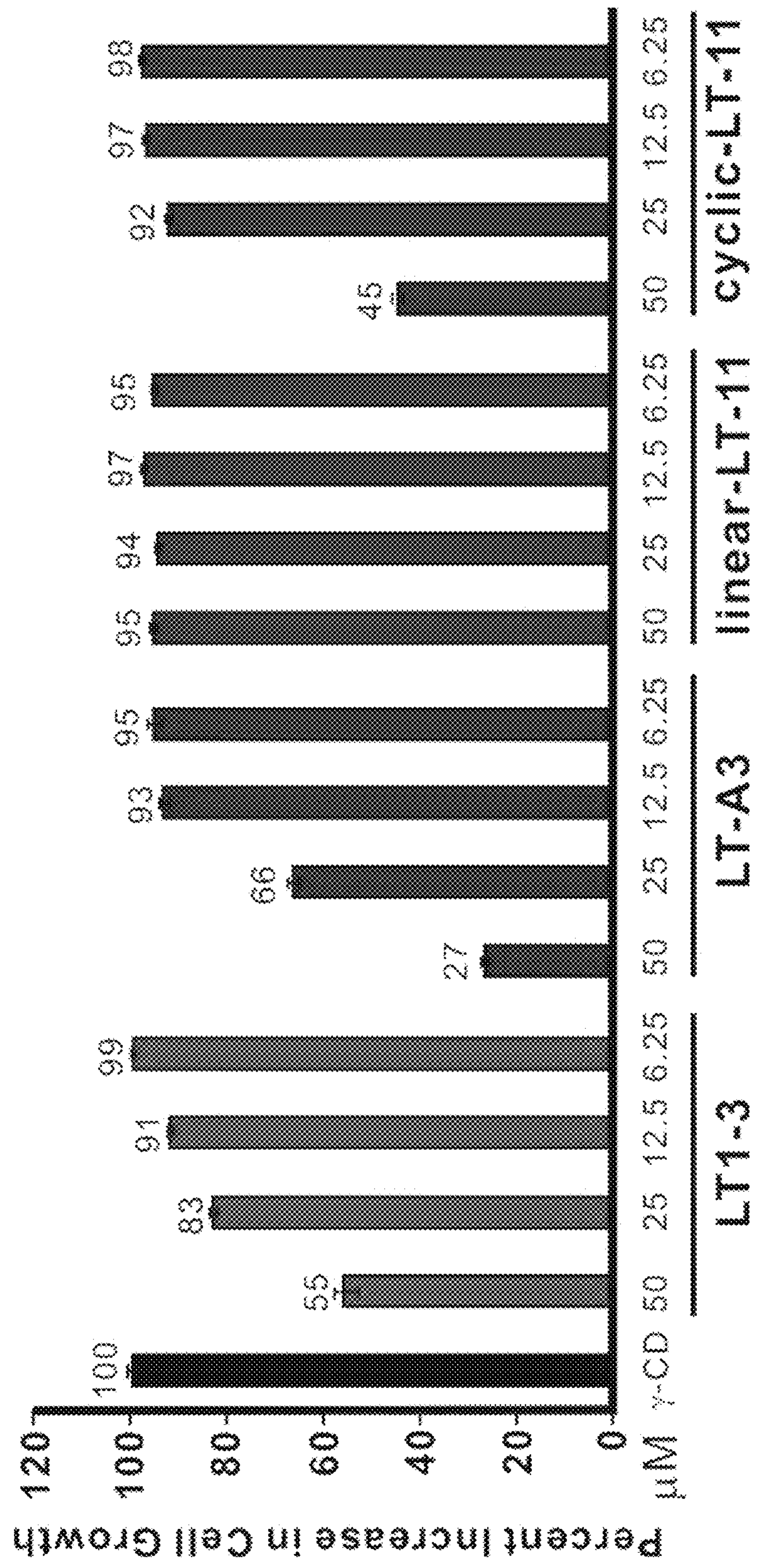
FIG. 3 shows dose effect of Fmoc-LT-peptides (LT-peptides) in growth inhibition in CL1-5 cells.
Figure 4:
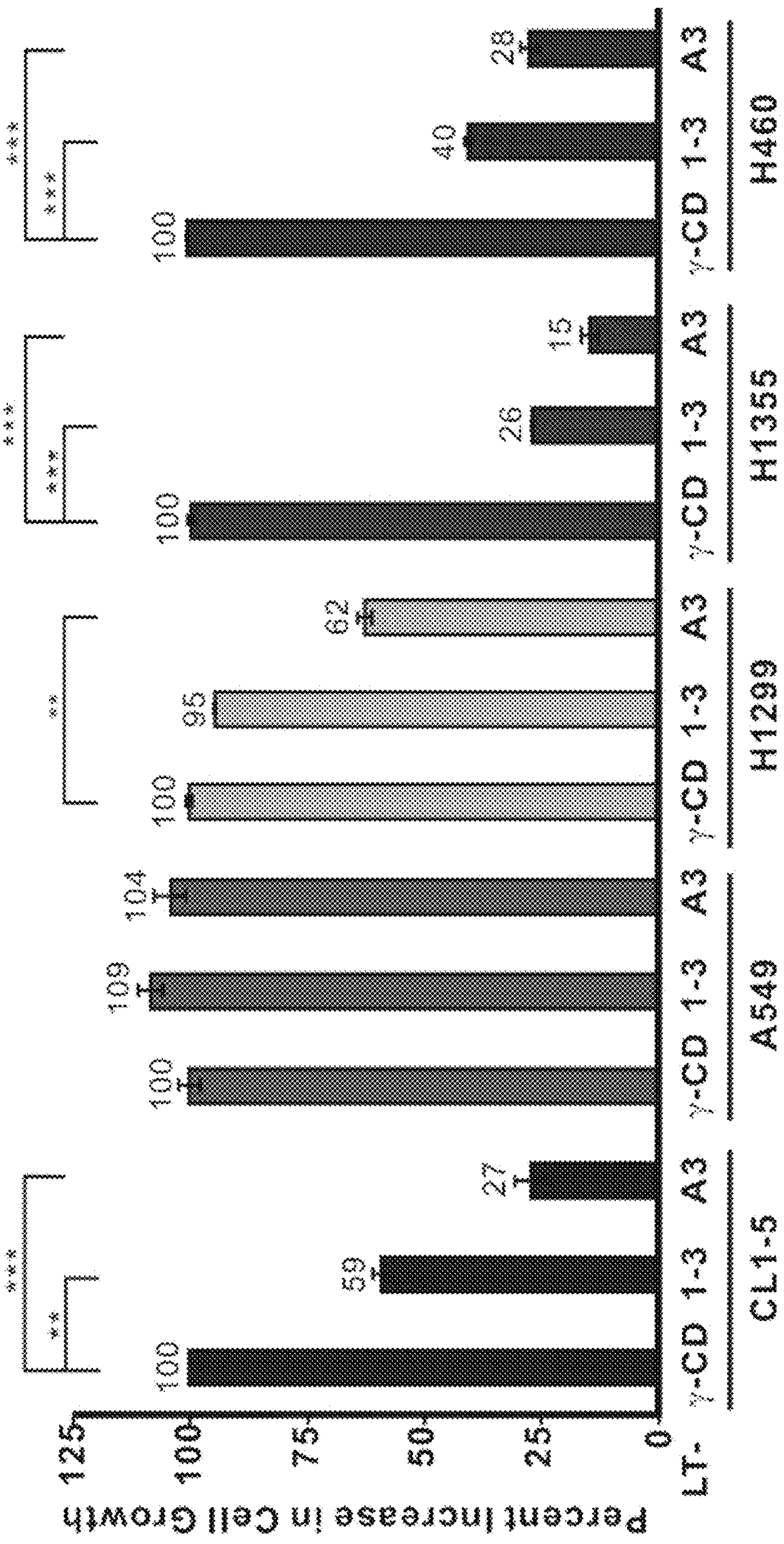
FIG. 4 shows growth inhibition activity of Fmoc-LT1-3 and Fmoc-LT-A3 in various lung cancer lines.

The results showed that Fmoc-LT-A3 had the best growth inhibition capability. F-moc-LT-A1, LT-A2, LT-A4, LT-A6, and LT-A7 also had better inhibition activity than F-moc-LT1-3 peptide (FIG. 1). Further modifications on LT-A3 peptide revealed less growth inhibition activities than Fmoc-LT-A3 peptide (FIG. 2). Dose effect experiment also demonstrated that Fmoc-LT-A3 has the best growth inhibition capability (FIG. 3). We also determined the effect of Fmoc-LT1-3 and Fmoc-LT-A3 on growth inhibition in different lung cancer cell lines. The results showed that Fmoc-LT1-3 and Fmoc-LT-A3 greatly inhibited CL1-5, H1355 and H460 lung cancer cell lines, partially inhibited H1299 cell line, and had no effect on A549 cell line (FIG. 4). The trends of growth inhibition are similar between Fmoc-LT1-3 and Fmoc-A3, suggesting that these two peptides function specifically in growth inhibition.

Example 3 Cell Invasion Assay

Figure 5:
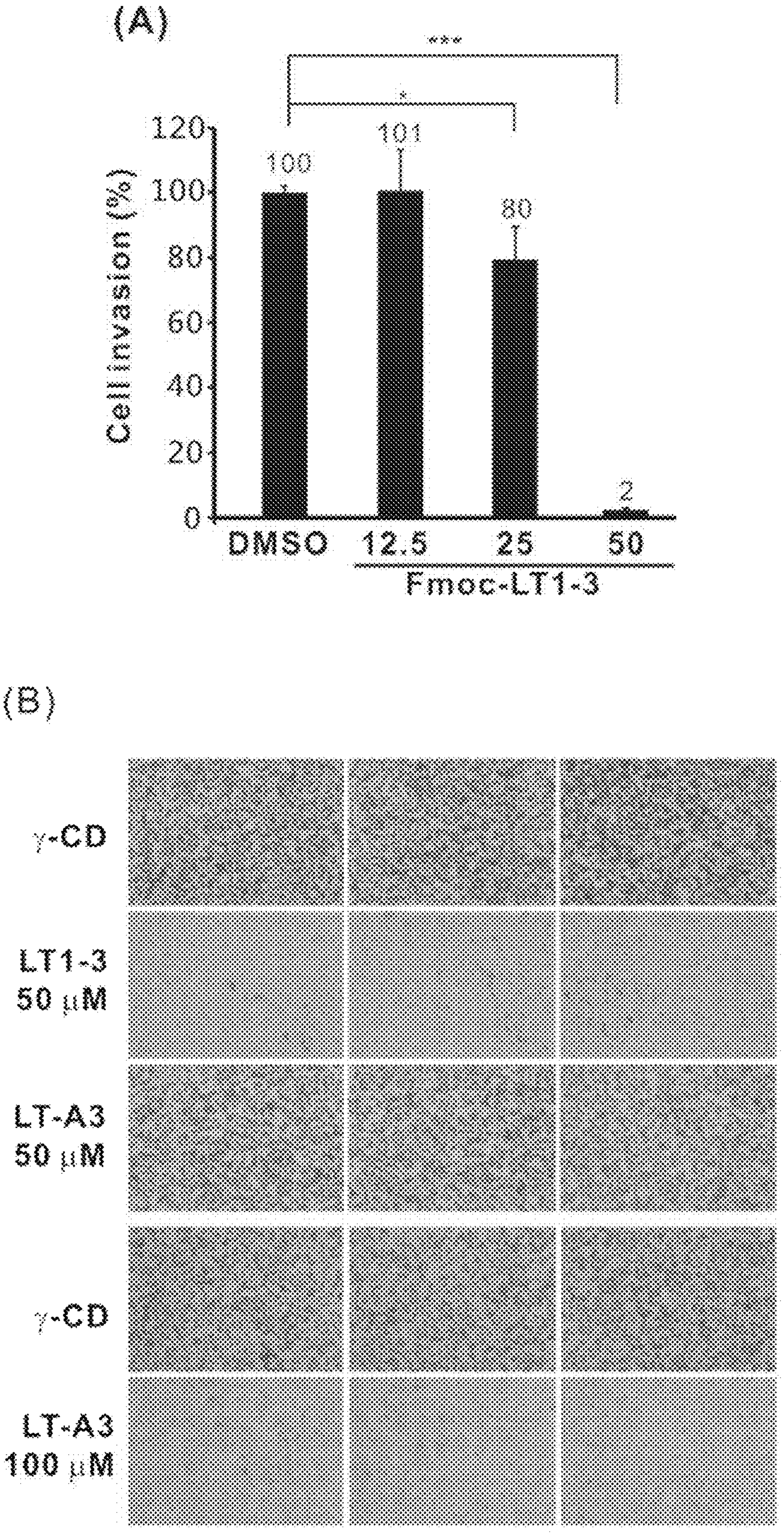
FIGS. 5(A) to (C) show dose effect of Fmoc-LT1-3 (A), Fmoc-LT-A3 (B) and Fmoc-LT-A3-PEG3 (C) on invasion inhibition.
Figure 5:
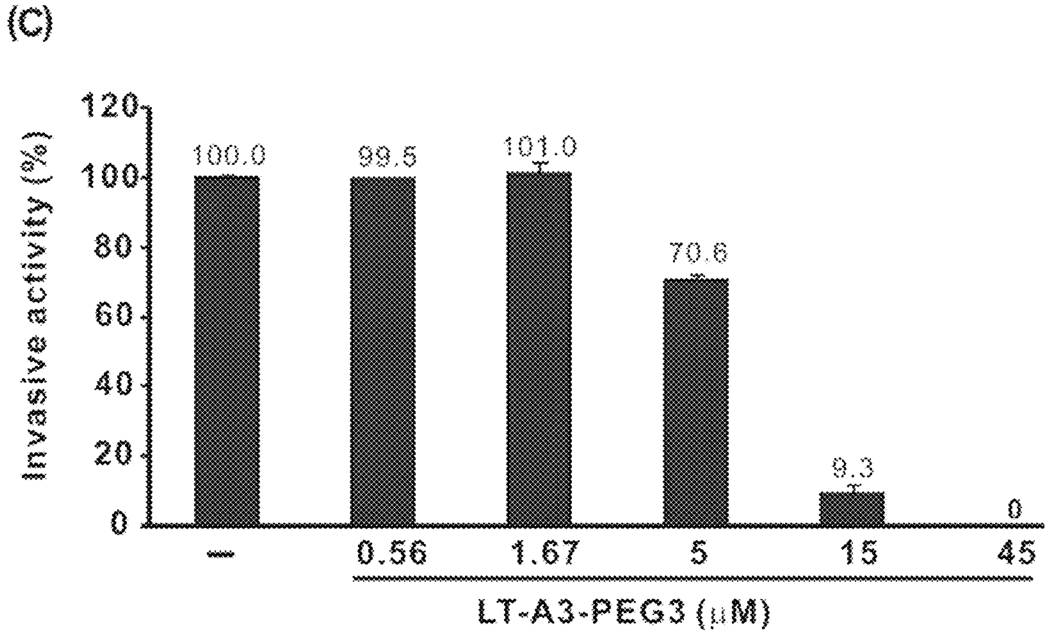

Fmoc-LT1-3 peptides were used in cell invasion assay. A 24-well modified Boyden chamber with a polycarbonate membrane (8-μm pore size) was used for in vitro invasion assays. The membrane was coated with 18 μg Matrigel (Becton Dickinson, diluted in RPMI-1640). CL1-5 cells ($3\times10^4$ cells/well) in RPMI medium with various concentrations of peptide were seeded onto the upper chamber. RPMI-1640 medium alone was used in the lower chamber. After 24 h of incubation, the cells were fixed with ice-cold 100% methanol and stained with 10% Giemsa. Following staining, cells on the upper side of the membrane were removed with a cotton swab. The number of invaded cells attached to the lower surface of the polycarbonate membranes was counted under a light microscope. All experiments were performed in triplicate. As shown in FIGS. 5A and 5B, both Fmoc-LT1-3 and Fmoc-LT-A3 inhibited cell invasion, however Fmoc-LT1-3 had better invasion inhibition capability than Fmoc-LT-A3. Interestingly, C-terminal PEGylation on Fmoc-LT-A3 greatly increased invasive inhibition activity (FIG. 5C).

Figure 6:
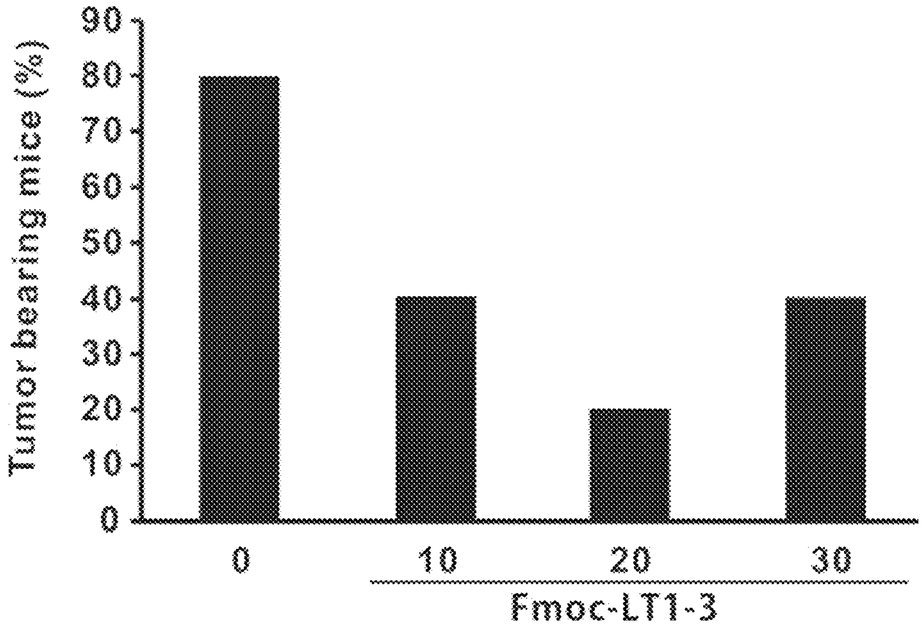
FIG. 6 shows early tumor formation rate in mice treated with different amount of LT1-3 peptide at day 18.
Figure 9:
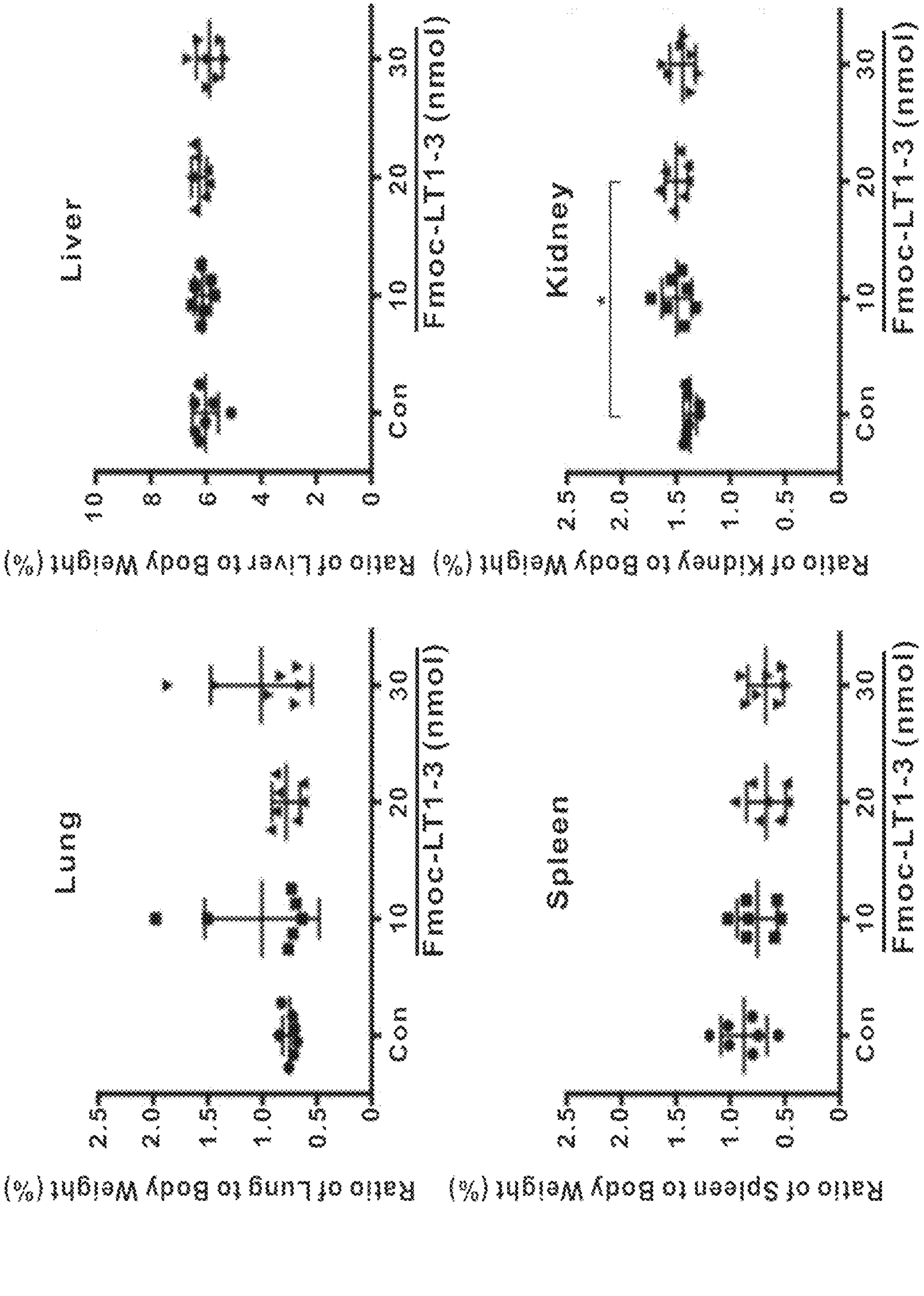
FIG. 9 shows relative organ weight of animal treated with different levels of Fmoc-LT1-3.

Example 4 the Effect of Fmoc-LT1-3 on Tumor Growth in Xenograft Animal Model Six-week old immune deficient BALB/CAnN.Cg-Foxn1nu/CrlBltw mice were housed in individual ventilated chambers (IVC). A total of $2\times10^6$ CL1-5 lung cancer cells in 100 μL PBS were mixed with 100 μL of 10× Matrigel. The lung cancer cells/Matrigel mix was injected subcutaneously to the lower back of the mice. Three days later, the mice were treated with 0, 10, 20, or 30 nmol of Fmoc-LT-1-3 subcutaneously everyday. The Fmoc-LT-1-3 peptide was dissolved in 100% DMSO and diluted to the desired concentration in PBS from day 3 to day 17. On the $18^{th}$ day, we observed that 80% of control group animal, 40% of 10 nmol group animal, 20% of 20 nmol group animal, and 40% of 30 nmol group animal developed tumor. Percent of tumor free animal increased with increasing level of Fmoc-LT1-3 between 10 nmol and 20 nmol. However, 30 nmol group did not exhibit further increased percent of tumor free animal (FIG. 6). This phenomenon may be due to lower solubility of Fmoc-LT1-3 at higher concentration. We thus decided to replace the solvent from DMSO with γ-CD, and diluted the peptide to the desired concentration for injection on the $18^{th}$ day and thereafter. The volume of tumor was measured periodically. The results showed that 20 nmol of Fomc-LT1-3 has greatest effect on inhibiting tumor growth (FIG. 7). Although 10 nmol and 30 nmol of Fmoc-LT1-3/DMSO had the same initial tumor developing rate by day 18 as shown in FIG. 6, 30 nmol of Fmoc-LT1-3/γ-CD treatment group significant suppressed tumor growth after replacement the solvent with γ-CD (FIG. 7). On the $39^{th}$ day, animals were sacrificed. The tumor and organs were weighted, fixed and embedded in paraffin. Embedded tissue were sectioned and stained with hematoxylin-eosin for histologic analysis. As shown in FIG. 8, 20 nmol and 30 nmol of Fmoc-LT-1-3 significantly inhibited tumor weight when compared to the vesicle control group. FIG. 9 shows no significant differences of the relative weight of organs between treatment groups and the control group. The histologic analysis did not reveal obvious toxicity in animals when treated with Fmoc-LT1-3.

Example 5 the Effect of Fmoc-LT1-3 Peptide on Metastasis of Lung Cancer

Figure 10:
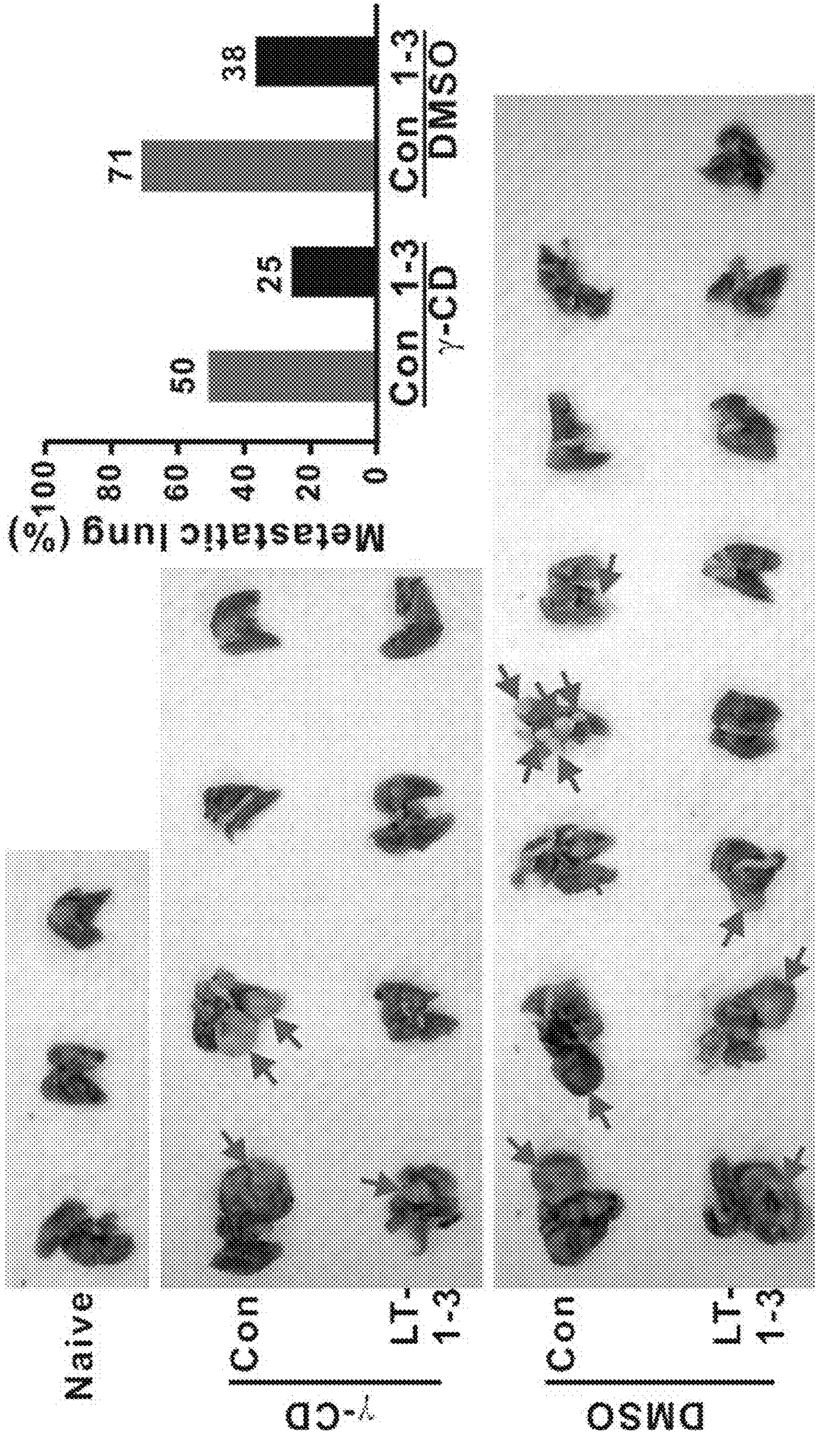
FIG. 10 shows the effect of Fmoc-LT1-3 on lung metastasis of CL1-5 cells injected through tail vein.

Five-weeks old immune deficient BALB/CAnN.Cg-Foxn1$^{nu}$/CrlBltw mice were housed in IVC. CL1-5 cells were pretreated with 200 μM Fmoc-LT1-3 for 24 h and then cultured in fresh medium containing Fmoc-LT1-3 peptide 6 h before cell harvest. CL1-5 cells were detached, centrifuged, and resuspended in PBS containing 200 μM Fmoc-LT1-3 peptide for injection. Thirty minutes before tail vein injection, the mice were also treated with 20 nmol Fmoc-LT1-3 subcutaneously. A total of $1\times10^6$ CL1-5 cells were intravenously injected into the mice. The second day after tail vein injection, 20 nmol of Fmoc-LT1-3/0.5% DMSO or Fmoc-LT1-3/γ-CD was subcutaneously injected into mice daily. By day 56, animals were sacrificed, and all organs were examined for metastasis formation. The metastatic nodules on the surface of lungs were counted under dissecting microscope. Organs were fixed and embedded in paraffin. Embedded tissue was sectioned and stained with hematoxylin-eosin for histologic analysis. As shown in FIG. 10, Fmoc-LT1-3 significantly inhibited metastasis of CL1-5 cells via tail vein injection in both solvents.

Example 6 Therapy of Fmoc-LT1-3 Peptide and Cisplatin

Figure 11:
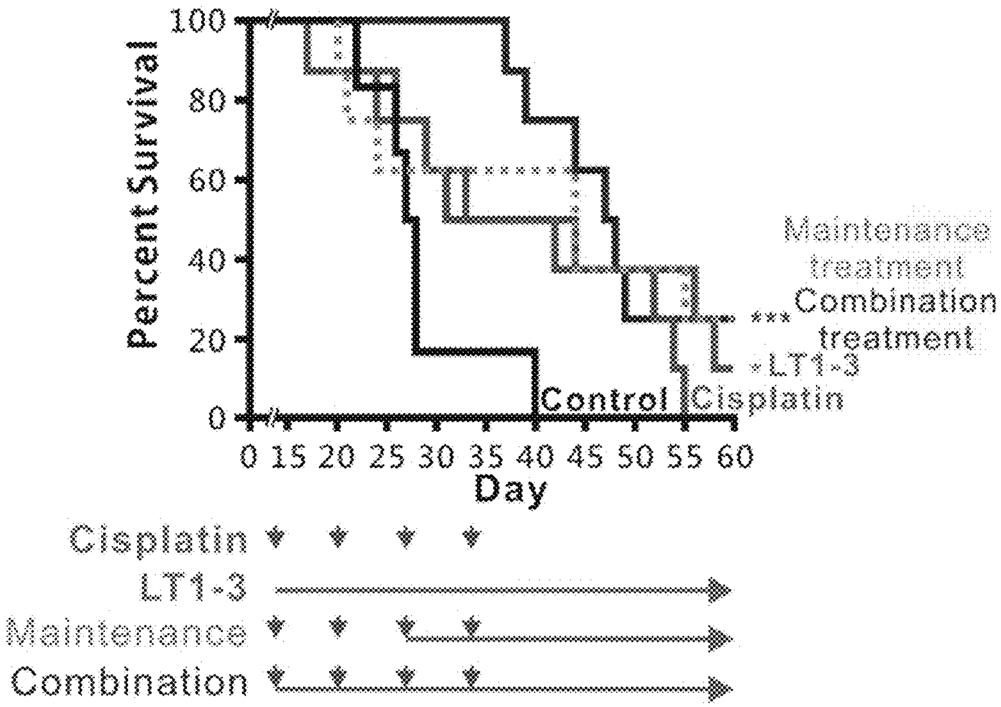
FIG. 11 shows survival proportions of control, CDDP, LT1-3, CDDP+LT1-3 for maintenance therapy and CDDP+LT1-3 for combined therapy.

CL1-5 cells were washed, detached, and resuspended in PBS. Subsequently, a single-cell suspension containing $2\times10^6$ cell in 80 μL PBS was mixed with 20 μL 10× Matrigel (Corning, 5117012). The cell suspension was subcutaneously injected into the upper back of the immune deficient BALB/CAnN.Cg-Foxn1nu/CrlBltw mice. The tumors were left to grow for 10 days, during which 90% of mice generated tumors. The tumor-bearing mice were divided into five groups (n=8/group). The average tumor volume was 120-140 $mm^3$ among five groups: Control, Fmoc-LT1-3, cisplatin, maintenance treatment and combined treatment. On day 13, the mice in the Fmoc-LT1-3 group were subcutaneously injected with 20 nmol Fmoc-LT1-3/γ-CD in the lower back daily. The mice in the cisplatin group were administered an intraperitoneal injection (IP) of 4 mg/kg cisplatin every week, 4 times in total. The mice in maintenance treatment group received IP of cisplatin 4 times and 20 nmol of Fmoc-LT1-3/γ-CD daily at the third IP injection of cisplatin. The mice in the combined treatment group were administered IP of cisplatin weekly 4 times and 20 nmol Fmoc-LT1-3/γ-CD daily. During the course of each treatment, the tumor volume was measured every 3 days. The mortality rates of mice were recorded, which included mice with tumor volume over 1500 $mm^3$. The percent of survival rate is recorded in FIG. 11 and the median survival of each group is calculated in Table 1. The results showed that the median survival of vesicle control group was 27.5 days, cisplatin only and Fmoc-LT1-3 only groups extended median survival to 37.5 days, the combination treatment with cisplatin and Fmoc-LT1-3 further extended median survival to 47.5 days, and the maintenance treatment group also extended median survival to 44 days. Interestingly, Fmoc-LT1-3 seemed to alleviate cisplatin-induced toxicity as we observed that mice died after cisplatin injection in cisplatin only group and the first two cycles of maintenance groups but not in the combination treatment group (FIG. 11). In addition, the mice in combination treatment were more active and healthier than the cisplatin only group. Thus, Fmoc-LT1-3 not only inhibits tumor growth and metastasis but also reduces toxicity of cisplatin and significantly enhances animal survival in combination treatment with cisplatin.

TABLE 1

Fmoc-LT1-3 peptide elongates animal survival in combination with cisplatin treatment and in maintenance therapy.

| | Con | CDDP | LT | Combination treatment | Maintenance treatment |
|---|---|---|---|---|---|
| Median survival (day) | 27.5 | 37.5 | 37.5 | 47.5 | 44.0 |

Example 7 Cell Proliferation and Invasion Assays of the Fragments within LT (SEQ ID NO:1)

Figure 12:
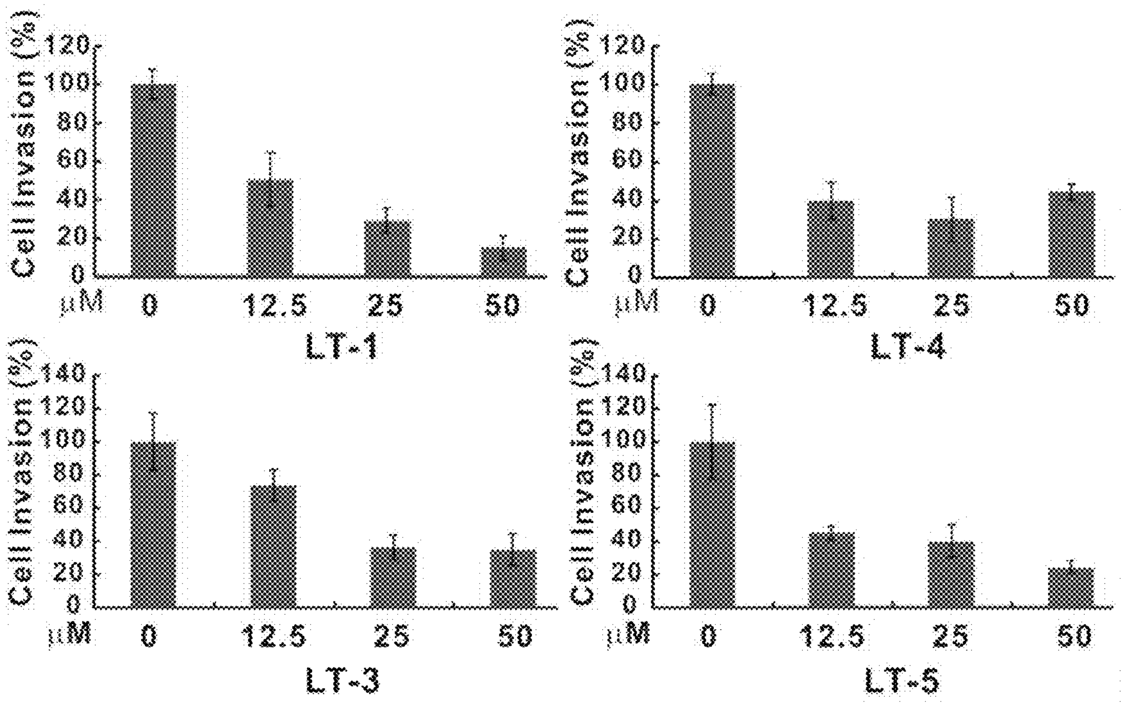
FIG. 12 shows the effect of LT-1, -3, -4, -5 on invasion inhibition of CL1-5 cells.

The cell proliferation assay and invasion assay of the peptide fragments LT-1, LT-2, LT-3, LT-4 and LT-5 at the concentrations of 0 μM, 12.5 μM, 25 μM and 50 μM were assayed according to the method described in Examples 2 and 3. LT-1 possesses an inhibitory effect on growth and invasion activity while LT-3, LT-4 and LT-5 have the inhibitory effect on cell invasion only. Due to cyclization effect during peptide synthesis, no full-length LT-2 peptide was obtained for final analysis. However, the N-terminal sequence of LT-2 contains the sequence of LT1-3, and thus it is highly possible that LT-2 has the inhibitory effect on growth and invasion activity (see FIG. 12 and the table

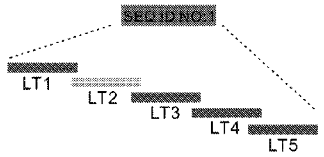

below).

TABLE 2

| The role of LT-1, -3, -4, -5 in growth and invasion inhibition of CL1-5 cells. | | |
|---|---|---|
| | Growth inhibition | Invasion inhibition |
| LT-1 | Yes | Yes |
| LT-3 | No | Yes |
| LT-4 | No | Yes |
| LT-5 | No | Yes |

Example 8 the Effect of LT-Peptides on Cell Invasion in CL1-5 Lung Cancer Cells

Figure 13:
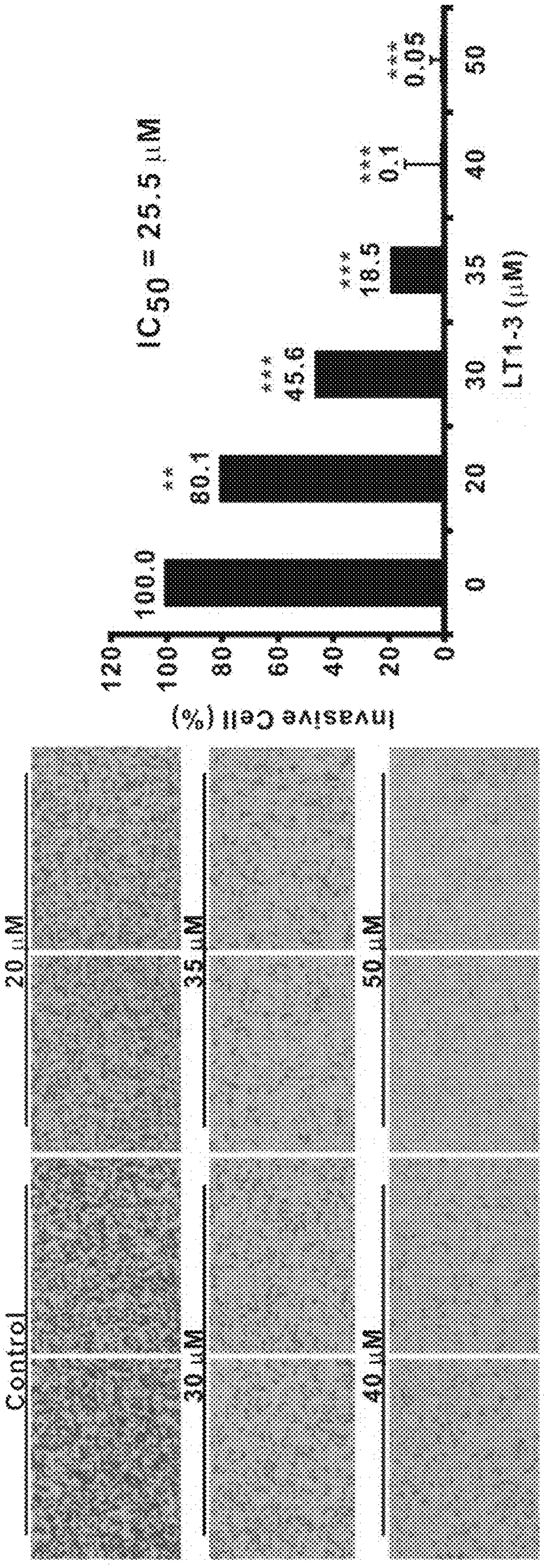
FIG. 13 shows the effect of LT1-3 peptide on cell invasion inhibition in CL1-5 cells.
Figure 14:
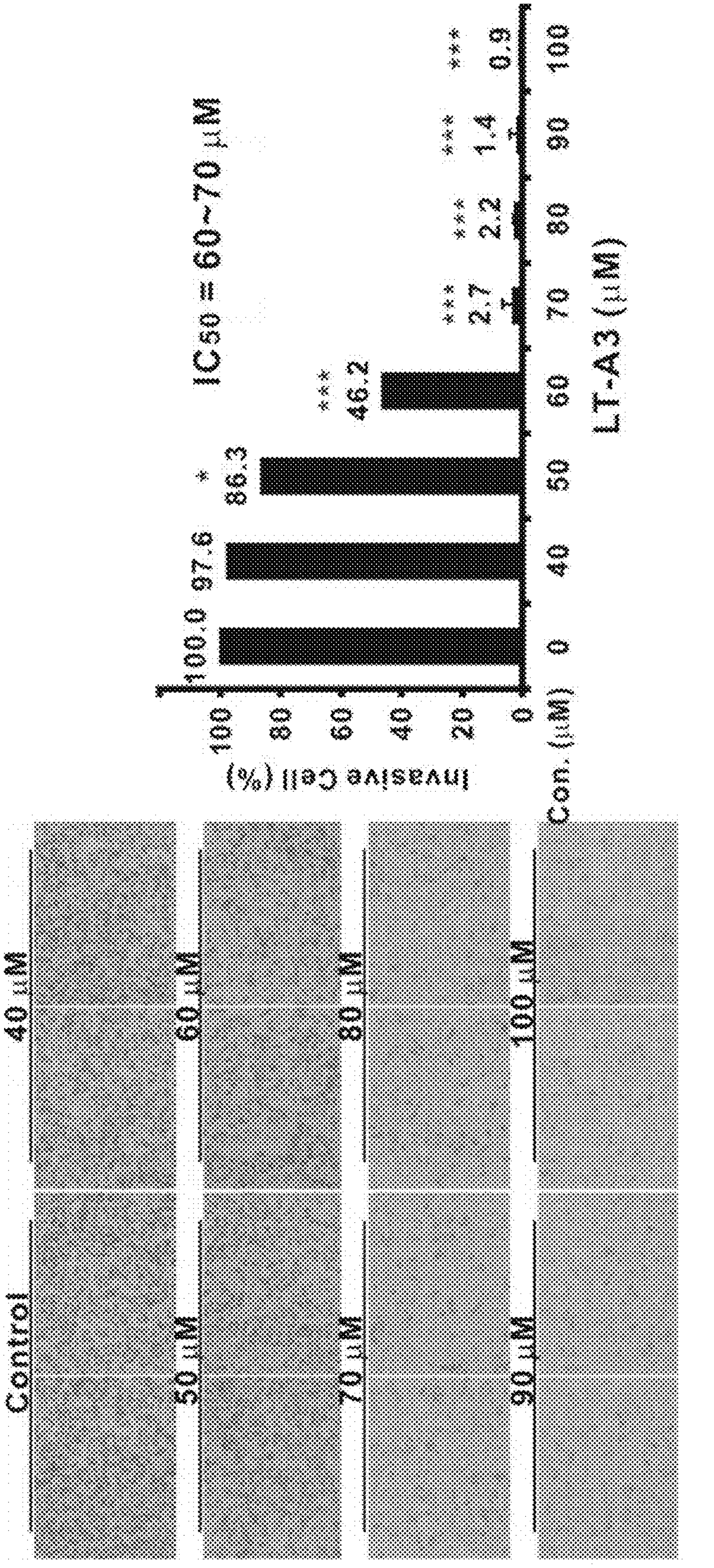
FIG. 14 shows the effect of LT-A3 peptide on cell invasion inhibition in CL1-5 cells.
Figure 15:
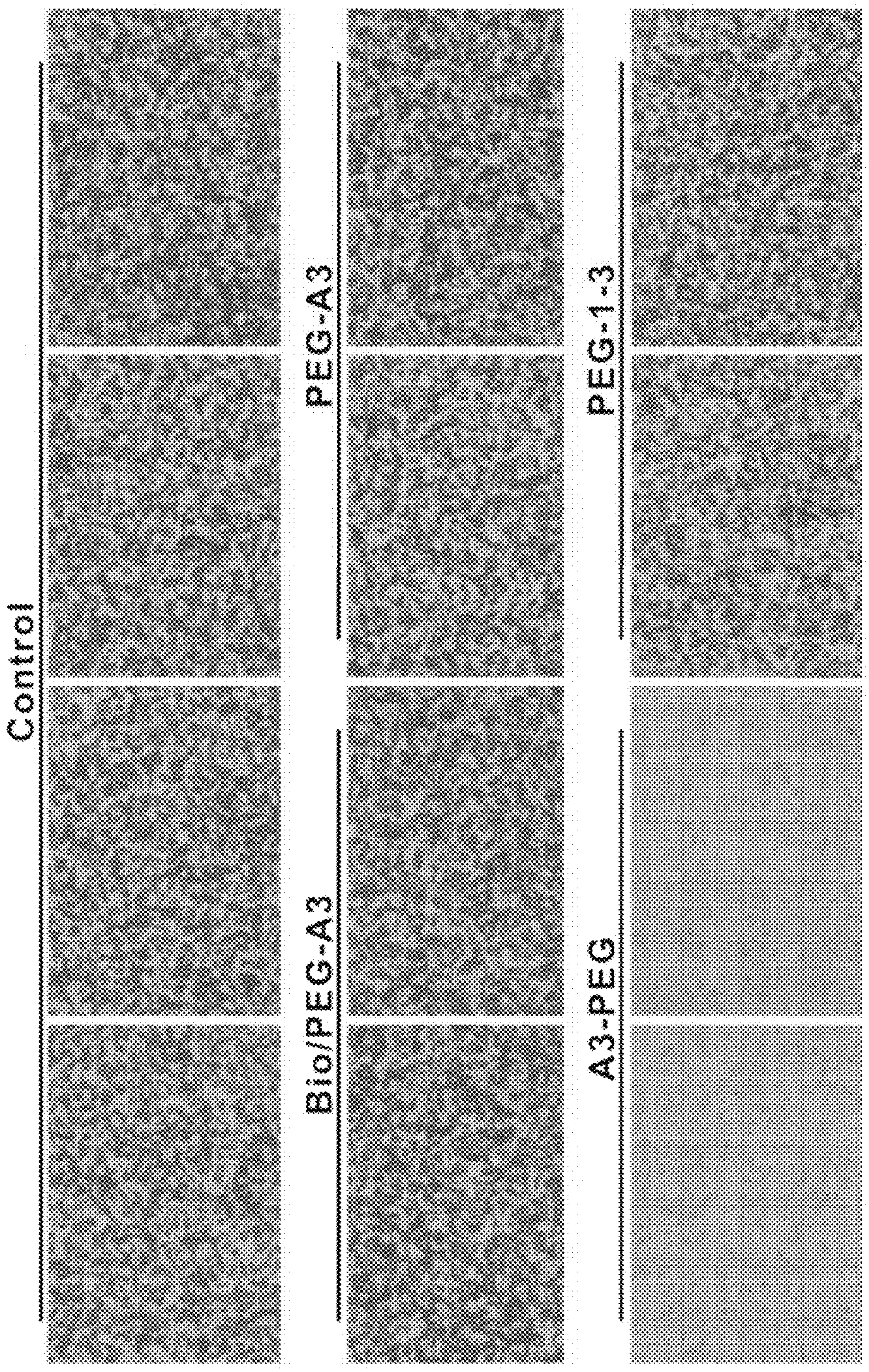
FIG. 15 shows the effect of N- or C-terminal modification of C-peptides on cell invasion in CL1-5 cells.
Figure 16:
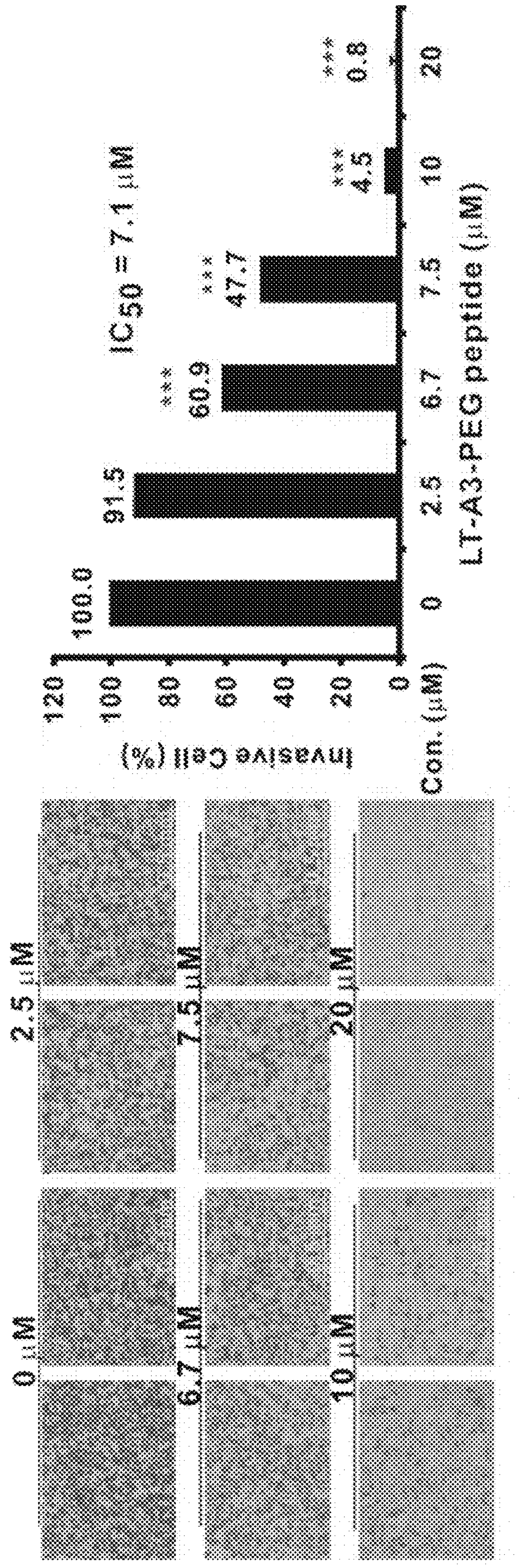
FIG. 16 shows the effect of LT-A3-PEG peptide on cell invasion in CL1-5 cells.
Figure 17:
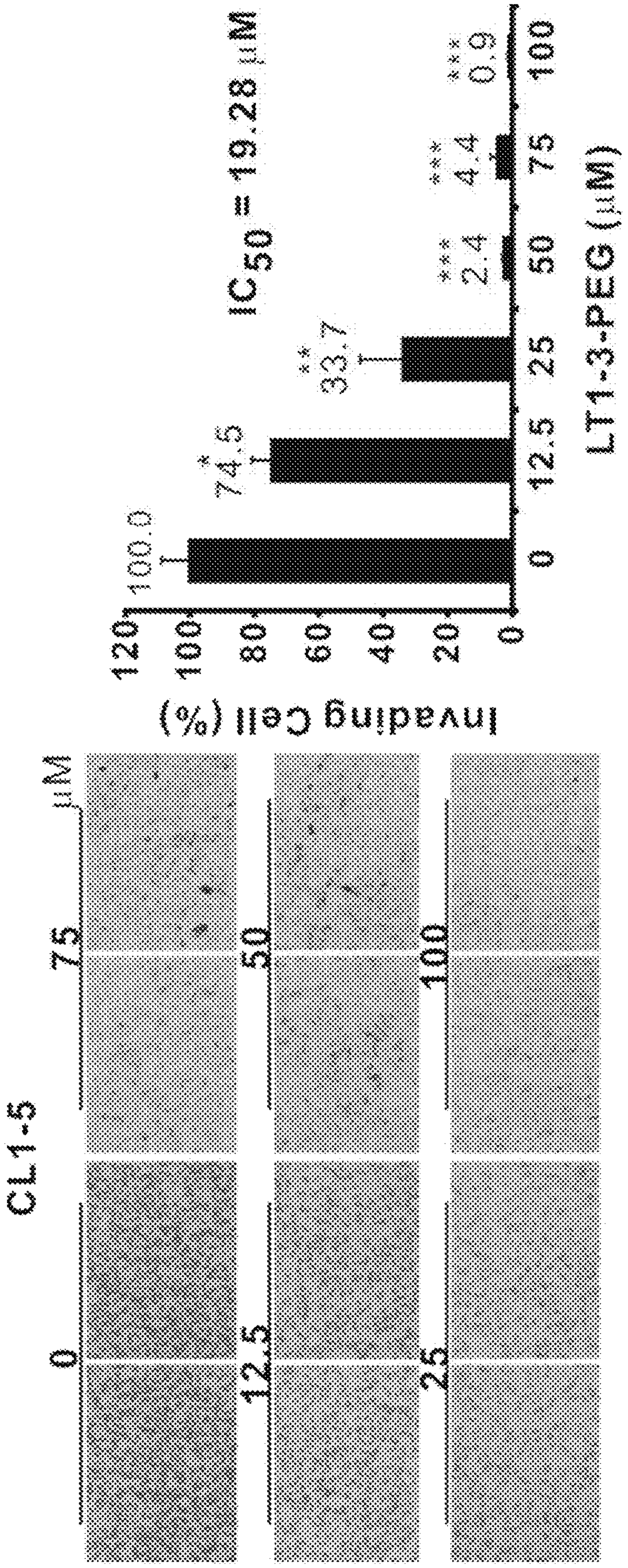
FIG. 17 shows the effect of LT1-3-PEG on cell invasion in CL1-5 cells.

LT1-3 and LT-A3 are hydrophobic. LT-A3 has better growth inhibition activity than LT1-3 (FIG. 1), while LT1-3 has better cell invasion inhibition than LT-A3 (FIG. 13 and FIG. 14). To increase peptide solubility PEG modification was applied on either N- or C-terminal of LT1-3 and LT-A3. The results showed that PEG3 modification on N-terminal of LT-1-3 and LT-A3 peptides (PEG-1-3 & PEG-A3) abolished invasion inhibition activity on CL1-5 cells while C-terminal PEG3 modification of LT-A3 (A3-PEG) had good invasion inhibition activity (FIG. 15). Dose effect of LT-A3-PEG on invasion inhibition of lung cancer cells revealed that LT-A3-PEG greatly enhanced invasion inhibition activity of the peptide (FIG. 16) when compared with LT-A3 (FIG. 14). C-terminal PEG3 modified LT-1-3 (LT1-3-PEG) also enhanced invasion inhibition activity (FIG. 17) when compared with LT1-3 (FIG. 13).

Figure 18:
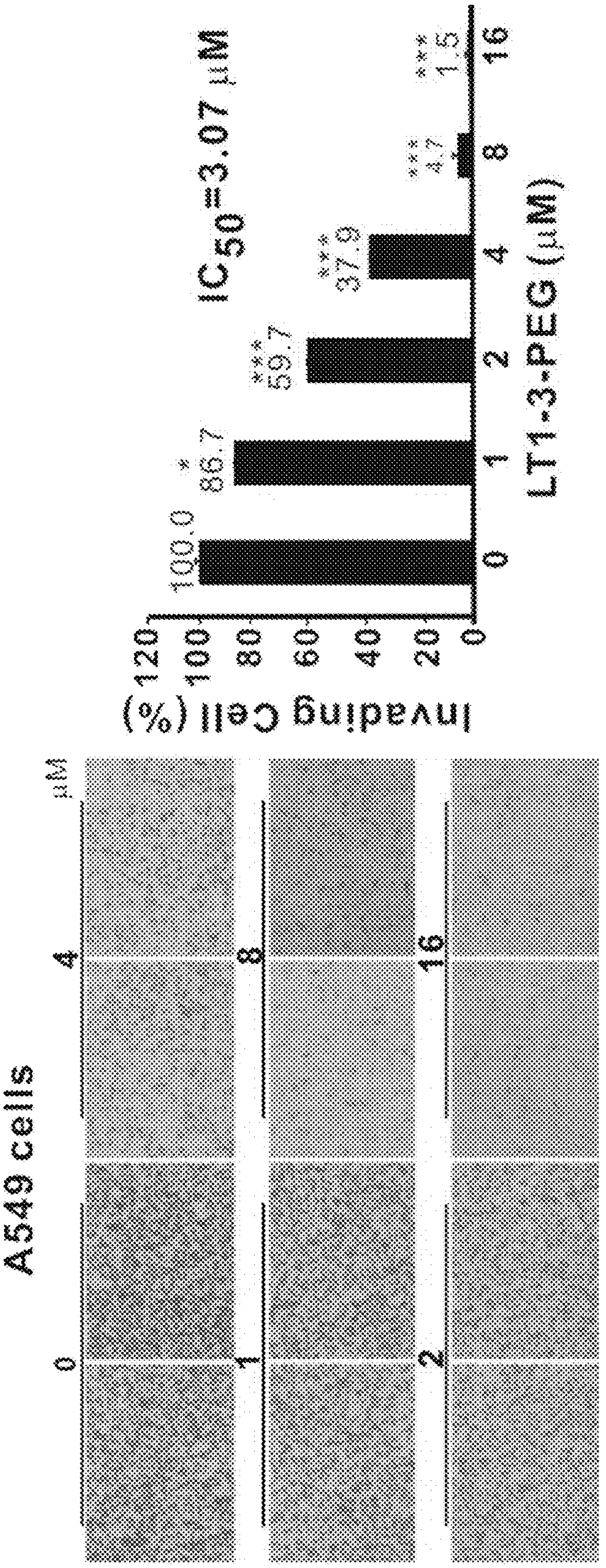
FIG. 18 shows the effect of LT1-3-PEG on cell invasion in A549 cells.
Figure 19:
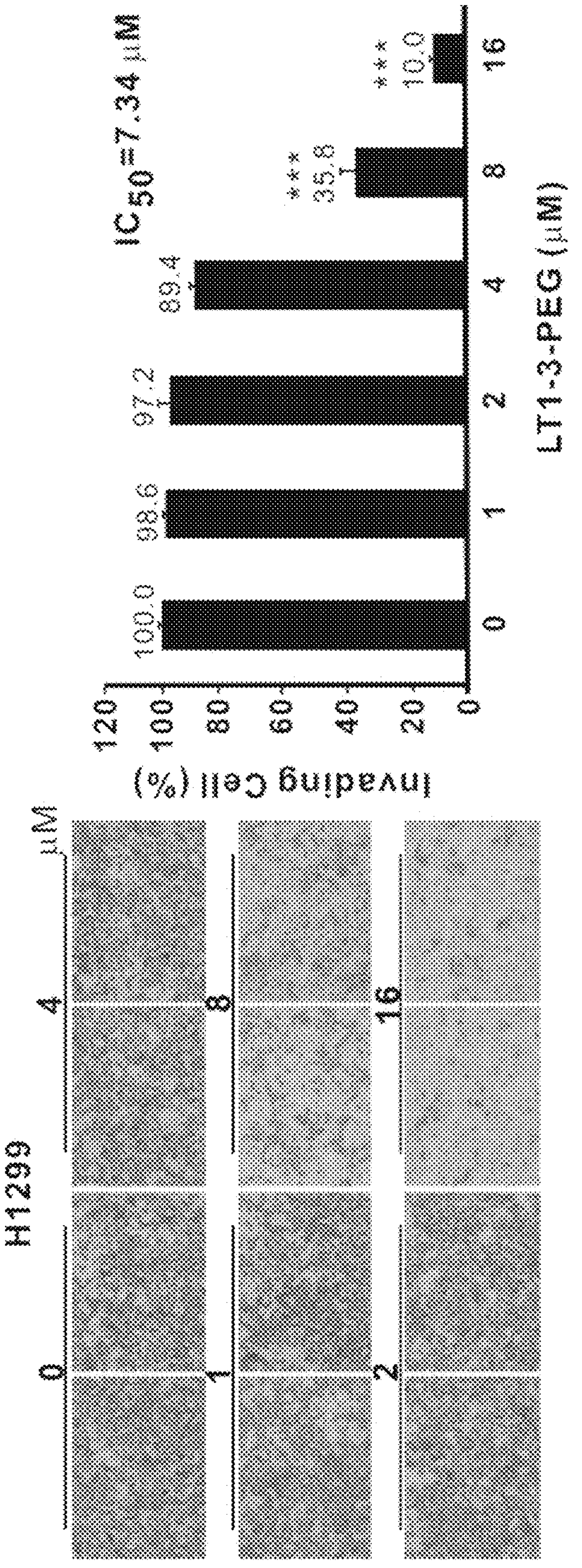
FIG. 19 shows the effect of LT1-3-PEG on cell invasion in H1299 cells.

Example 9 the Effect of LT-1-3-PEG on Cell Invasion in A549 and H1299 Lung Cancer Cells It is important to examine whether LT-peptides inhibit development of lung cancer cells other than CL1-5. The results showed that LT1-3-PEG also efficiently inhibited invasion of A549 and H1299 cells (FIGS. 18 and 19). LT1-3-PEG also inhibited invasion of H460 and H1355 lung cancer cells and the dose effect of LT1-3-PEG on these two cell lines are currently under investigation.

Figure 20:
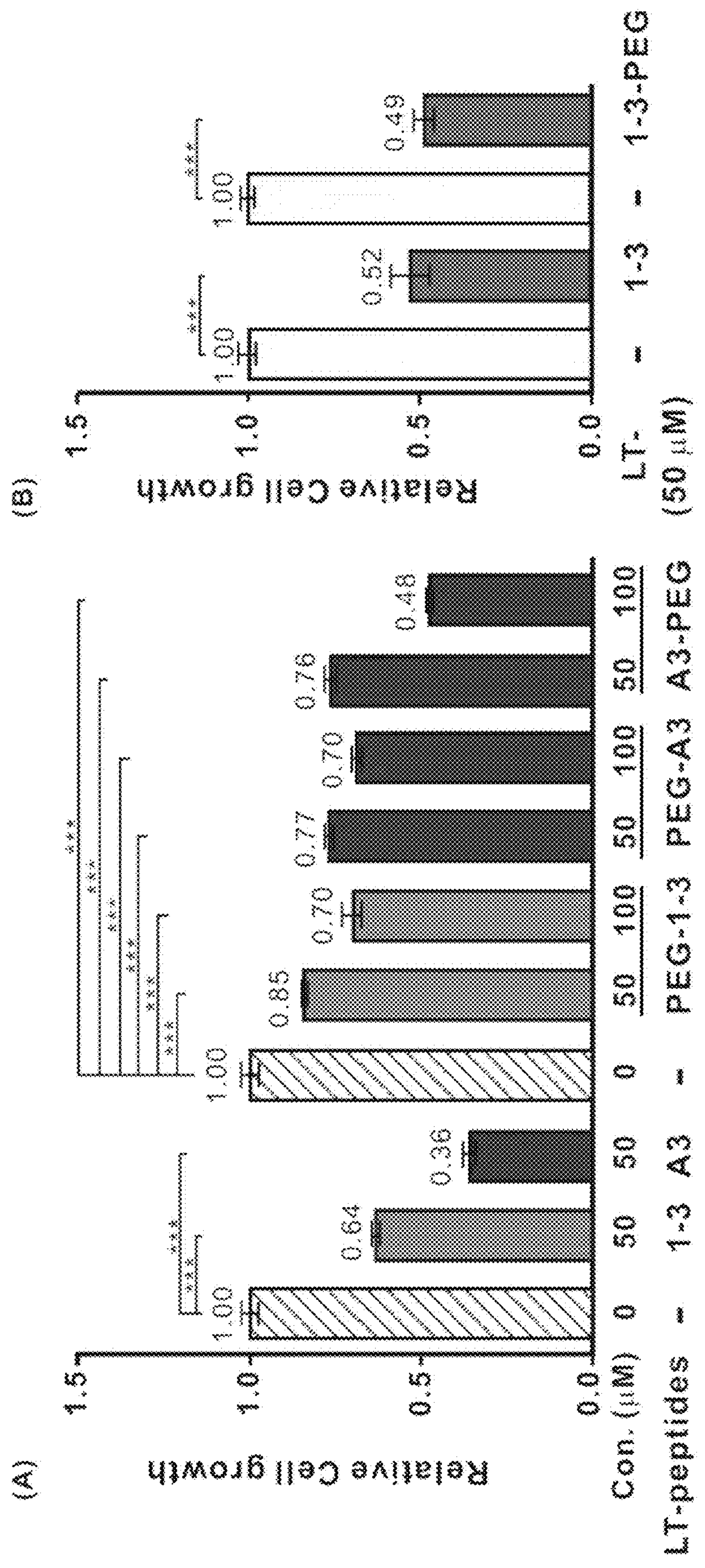
FIGS. 20(A) and (B) show the effect of N- or C-terminal modification of peptide on cell proliferation in CL1-5 cells; (A), PEG-LT1-3, PEG-LT-A3 and LT-A3-PEG; (B), LT1-3 and LT1-3-PEG.

Example 10 the Effect of PEG-Modified LT-Peptides on Cell Proliferation in CL1-5 Cells Although LT-A3 has great growth inhibition activity in CL1-5 cells, N-terminal or C-terminal PEG3 modification on LT-A3 (PEG-A3 & A3-PEG) and N-terminal PEG3 modification on LT1-3 (PEG-1-3) abolished growth inhibition activity (FIG. 20A). Fortunately, C-terminal PEG3 modified LT1-3 (LT1-3-PEG) retained growth inhibition activity (FIG. 20B).

Figure 21:
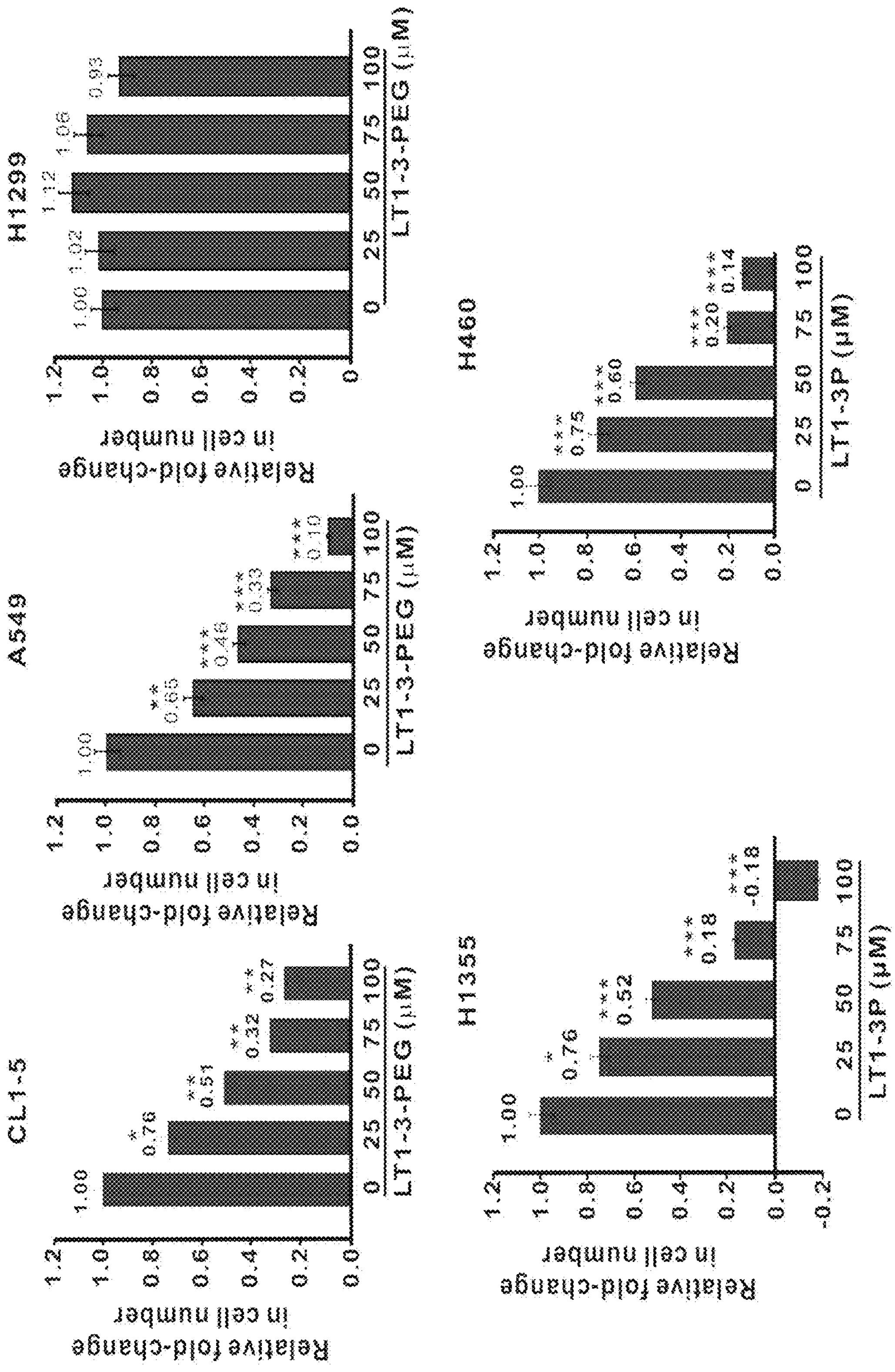
FIG. 21 shows the effect of LT1-3-PEG on proliferation of various lung cancer cell lines.

Example 11 the Effect of LT1-3-PEG on Cell Proliferation in Various Lung Cancer Cell Lines The dose effect of LT1-3-PEG on cell proliferation in various cell lines was examined. The results showed that LT1-3-PEG effectively inhibited CL1-5, A549, H460 and H1355 proliferation but not that in H1299 (FIG. 21).

Example 12 the Effect of LT-Peptides on Normal Cell Types

Figure 22:
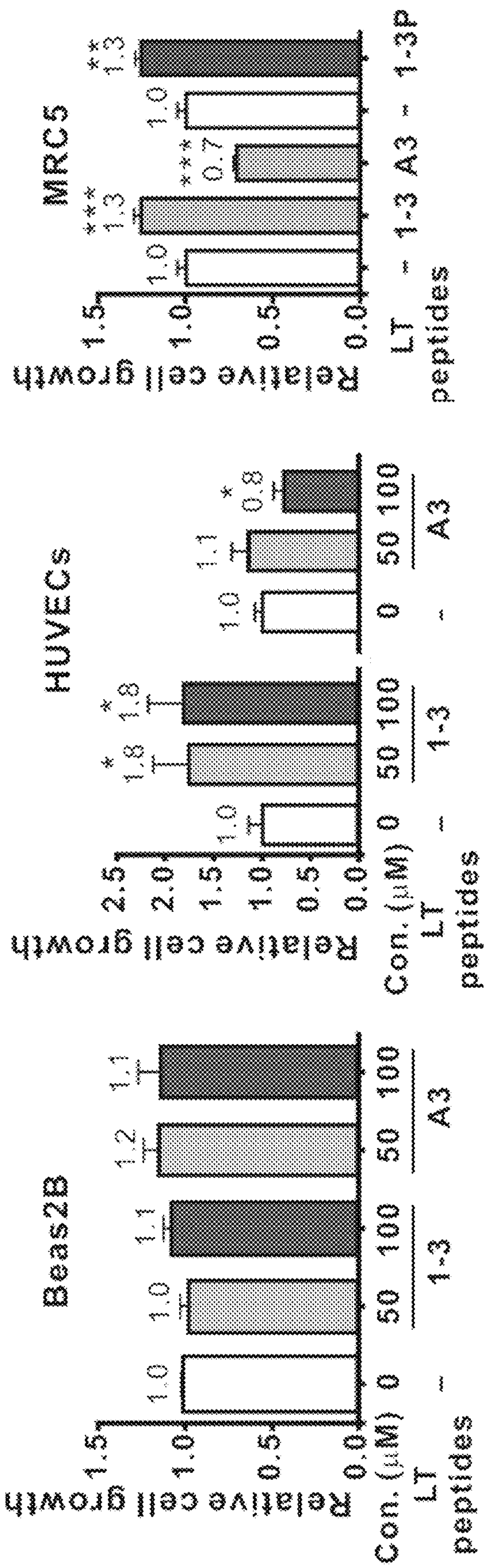
FIG. 22 shows LT1-3 does not inhibit growth of Beas2B, HUVECs and MRC5 normal cell lines.

It is important to investigate how LT-peptides affect normal cell lines. We treated SV40 transformed human bronchial epithelial cells Beas2B, human embryonic lung fibroblast MRC5, and HUVECs with LT-peptides and perform cell proliferation assay. Our preliminary results showed that LT-peptides did not inhibit growth of these normal cells (FIG. 22).

Example 13 the Effect of LT1-3-PEG on Proliferation of Breast Cancer Cells

Figure 23:
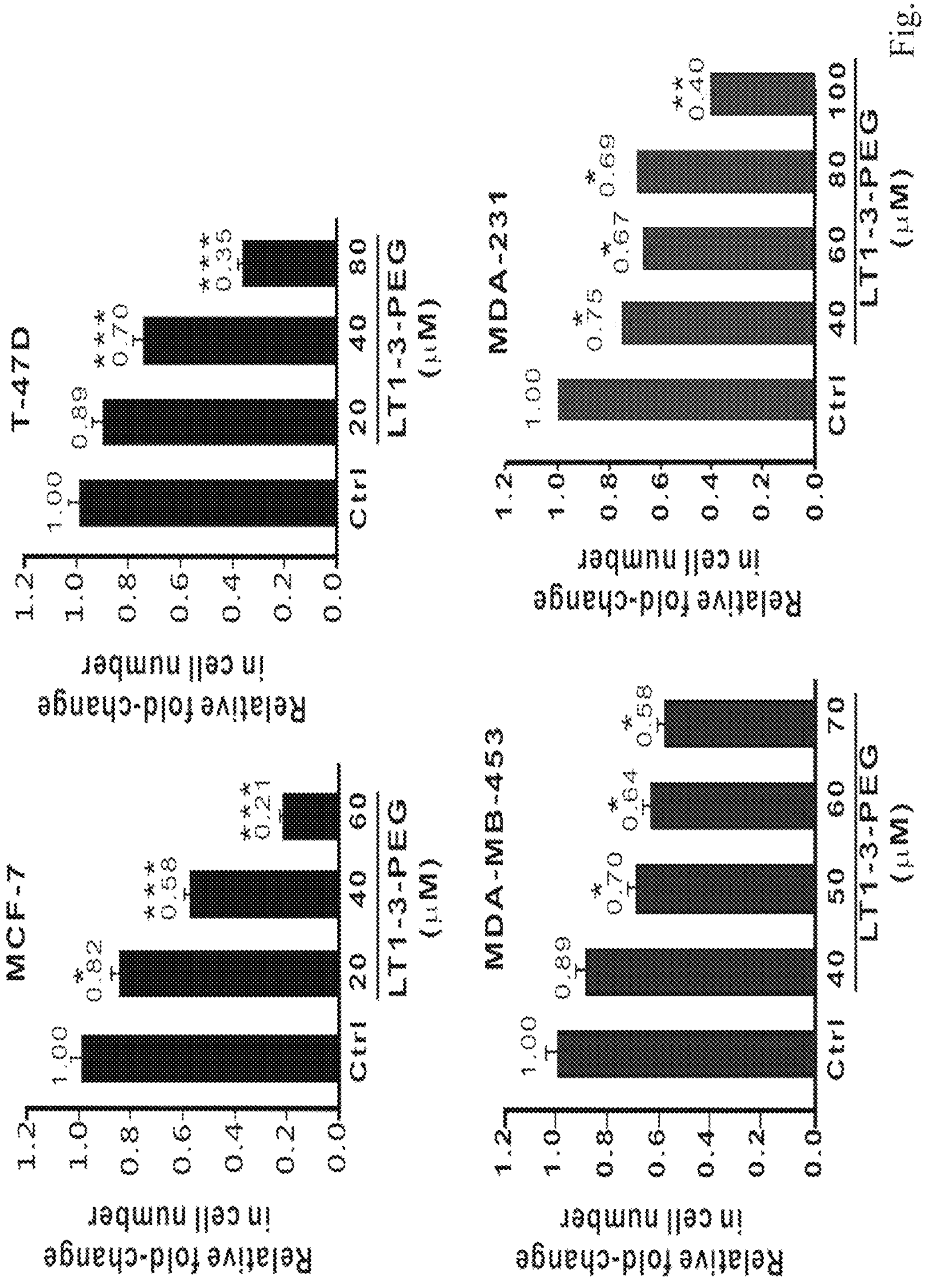
FIG. 23 shows the effect of LT1-3-PEG on proliferation of MCF-7, T-47D, MDA-MB-453 and MDA231 breast cancer cells.

LT1-3-PEG also inhibited proliferation of MCF-7, T-47D, MDA-MB-231 and MDA-MB-453 breast cancer cell lines (FIG. 23).

Figure 24:
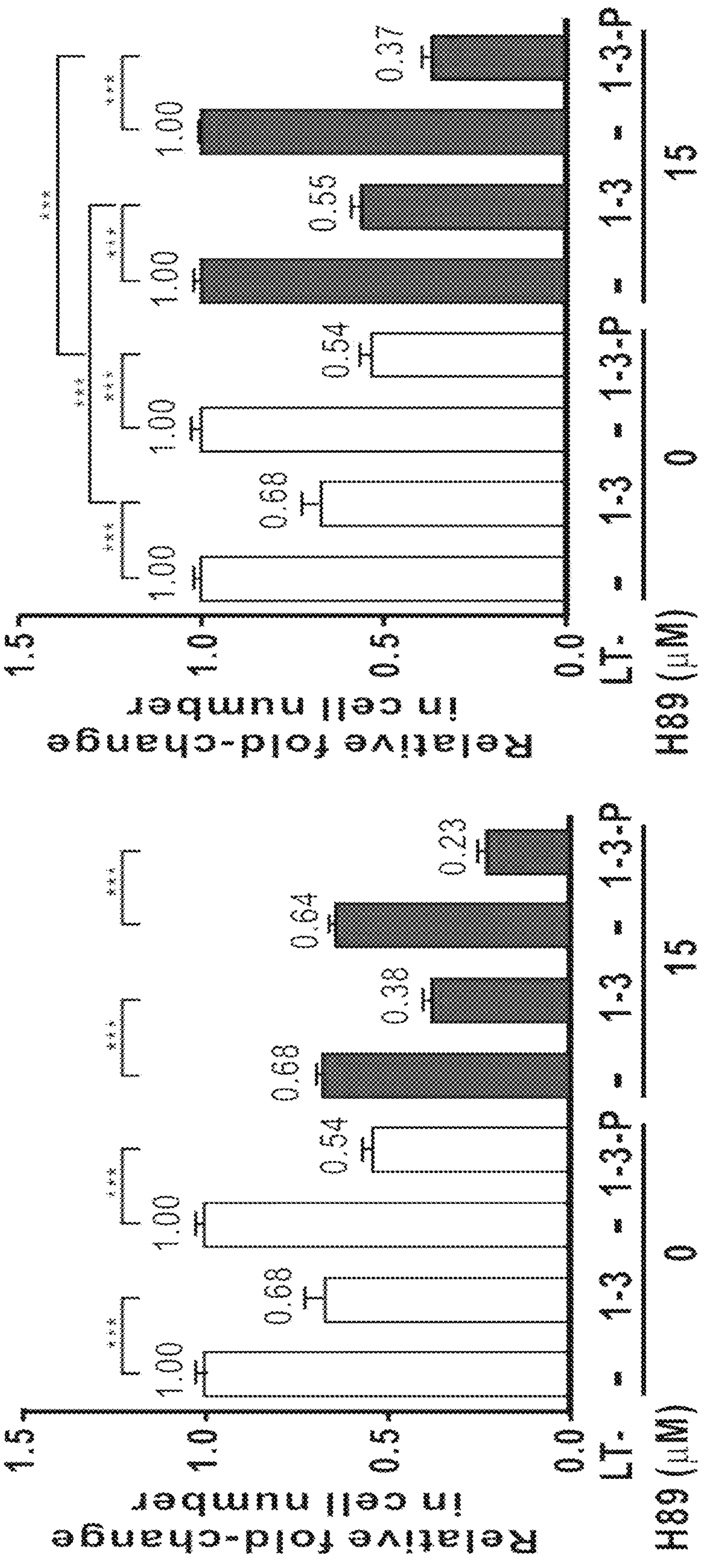
FIG. 24 shows that PKA inhibitor (H89) enhances growth inhibition activity of LT1-3 peptides on CL1-5 cells.
Figure 25:
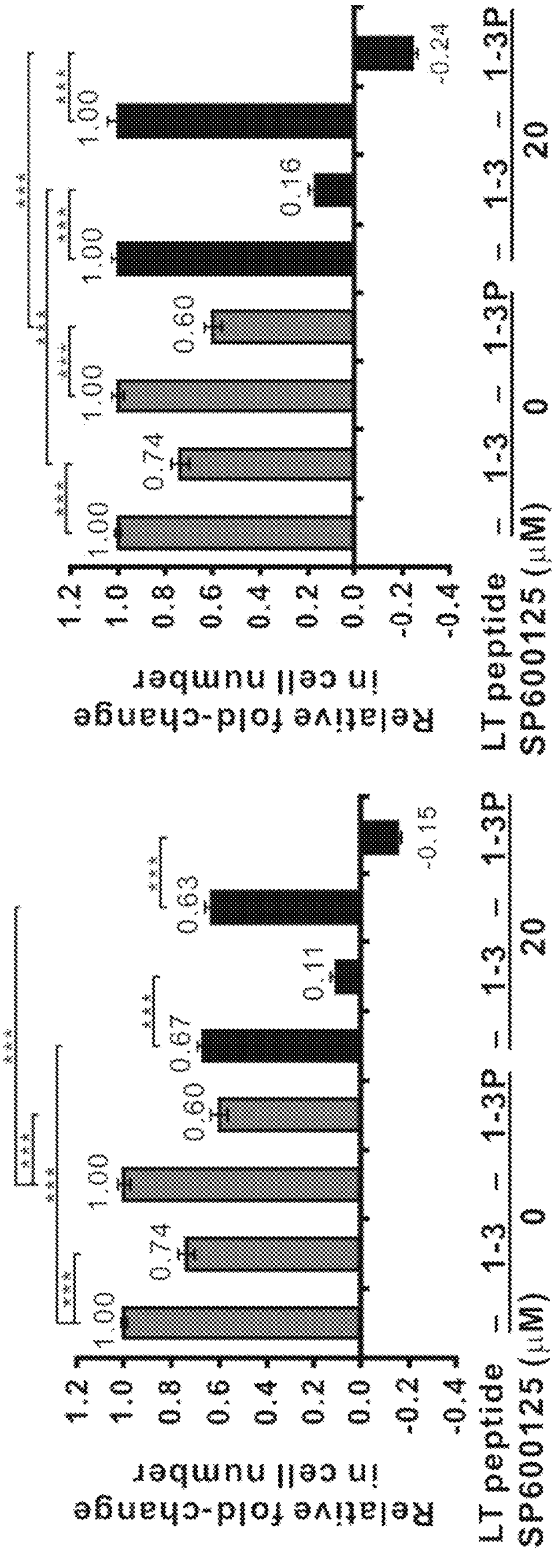
FIG. 25 shows that JNK inhibitor (Sp600125) enhances growth inhibition activity of LT1-3 peptides on CL1-5 cells.
Figure 26:
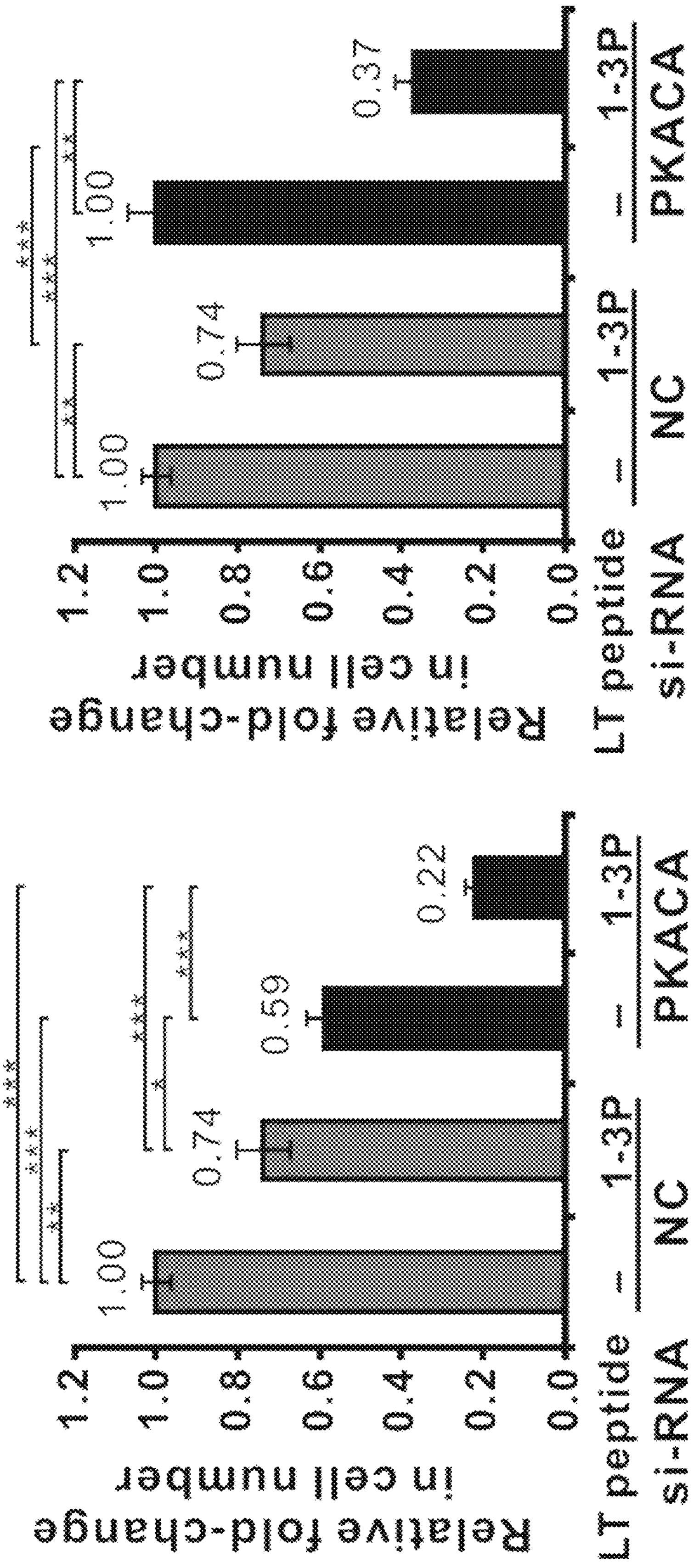
FIG. 26 shows that knockdown of the expression of PKACA enhances LT1-3-PEG-mediated growth inhibition activity on CL1-5 cells.
Figure 27:
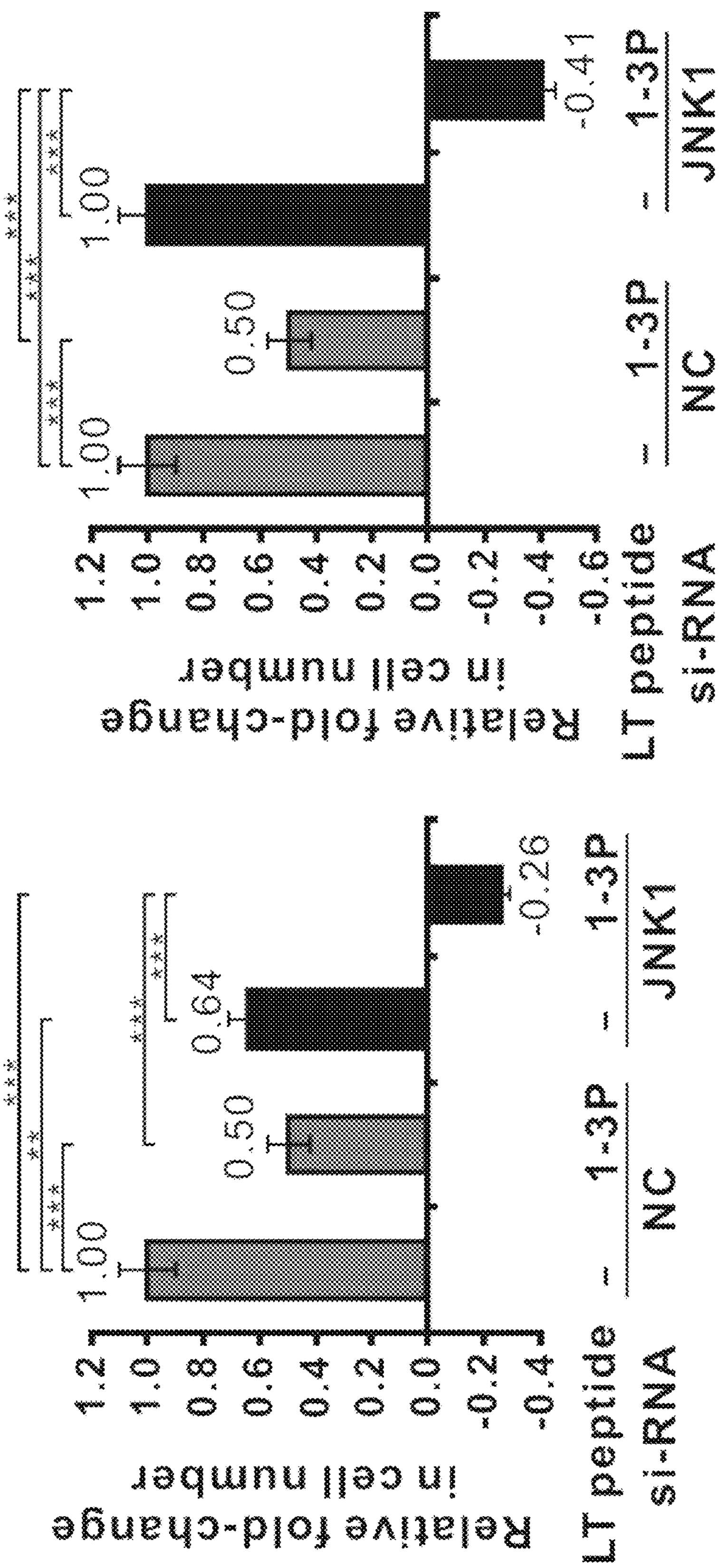
FIG. 27 shows that knockdown of the expression of JNK1 enhances LT1-3-PEG-mediated growth inhibition activity on CL1-5 cells.

Example 14 Blocking of PKA and JNK Activity Enhanced LT-Peptides-Mediated Growth Inhibition PKA inhibitor (H89) and JNK inhibitor (SP600125) enhanced LT1-3 and LT1-3-PEG-mediated growth inhibition in CL1-5 lung cancer cells (FIGS. 24 and 25). To confirm these observations, the catalytic subunit of PKA and JNK1 were interfered with siRNA in CL1-5 cells and the cells were followed by LT-peptides treatment. The results proved that decrease in the activity of PKA and JNK enhances an inhibitory effect on LT-1-3-peptides-mediated growth (FIGS. 26 and 27).

We claim:

1. A modified peptide comprising an amino acid sequence selected from a sequence consisting of the following:

ASAIYSVETINDGNFHIVELLALDQSLSLSVDGG-NPKIITNLSKQSTLNFDSPLYVGGMPG KSN-VASLRQAPGQNGTSFHGCIRNLYINSE (LT-1) (SEQ ID NO: 1), ASAIYSVETINDGNFHIVELLA (LT-1) (SEQ ID NO:2), FHIVELLA (LT1-3) (SEQ ID NO: 9), FHAVELLA (LT-A3) (SEQ ID NO:10), FKAVELLA (LT-K2) (SEQ ID NO:11), FRAVELLA (LT-R2) (SEQ ID NO:12), FHAVDLLA (LT-D5) (SEQ ID NO:13), FHAVHLLA (LT-H5) (SEQ ID NO:14), FHAVOrnLLA (LT-Orn5) (SEQ ID NO:15), AHAVE-LLA (LT-A13) (SEQ ID NO:16), FHAAELLA (LT-A34) (SEQ ID NO:17), FHAVEALA (LT-A36) (SEQ ID NO:18), FHAAEALA (LT-A346) (SEQ ID NO:19), FAIVALLA (LT-A25) (SEQ ID NO:20), FEAVHLLA (LT-E2H5) (SEQ ID NO:21), YHAVELLA (LT-Y1) (SEQ ID NO:22), WHAVELLA (LT-W1) (SEQ ID NO:23), FHAVELSA (LT-S7) (SEQ ID NO:24), FHAVELLS (LT-S8) (SEQ ID NO:25), DGNFHIV-ELLA (LT-11AA) (SEQ ID NO:26), AHIVELLA (LT-A1) (SEQ ID NO:27), FAIVELLA (LT-A2) (SEQ ID NO:28), FHIAELLA (LT-A4) (SEQ ID NO:29), FHIVALLA (LT-A5) (SEQ ID NO:30), FHIVEALA (LT-A6) (SEQ ID NO:31), or FHIVELAA (LT-A7) (SEQ ID NO:32), or a salt thereof, wherein the modified peptide has an improved stability or solubility compared to the unmodified peptide.

2. The modified peptide of claim 1, comprising an amino acid sequence consisting of FHIVELLA (SEQ ID NO:9) or FHAVELLA (SEQ ID NO:10); or a salt thereof.

3. The modified peptide of claim 1, wherein the modified peptide is a fluorenylmethyloxycarbonyl (Fmoc)-peptide, wherein Fmoc binds to N terminal or C terminal of the peptide selected from the group consisting of SEQ ID Nos: 9 to 32.

4. The modified peptide of claim 1, wherein the modified peptide is a PEG-peptide, wherein PEG binds to N terminal or C terminal of the peptide selected from the group consisting of SEQ ID Nos: 9 to 32.

5. The modified peptide of claim 1, wherein the modified peptide is cyclic peptide, wherein the cyclic peptide is DGNFHIVELLA (SEQ ID NO:26), wherein D bonds to A as head to tail cyclization.

6. A pharmaceutical composition, nanoparticle or liposome, comprising a modified peptide of claim 1 and a pharmaceutically acceptable carrier.

7. The pharmaceutical composition of claim 6, which further comprises a second anti-cancer agent.

8. The pharmaceutical composition of claim 7, wherein the second anti-cancer agent is erlotinib, afatinib, gefitinib, bevacizumab, ramucirumab, gefitinib, lapatinib, erlotinib, cisplatin, paclitaxel, methotrexate, cyclophosphamide, ifosfamide, chlorambucil, carmustine, carboplatin, vincristine, vinblastine, thiotepa, lomustine, semustine, 5-fluorouracil, corticosteroids, calcineurin inhibitors, NSAIDs, inhibitors of 5-lipoxygenase, or cytarabine.

9. A method for treating and/or ameliorating lung or breast cancer or inhibiting lung or breast cancer growth, invasion and/or metastasis, comprising administering an effective amount of a modified peptide of claim 1 or a salt thereof to a subject in need thereof.

10. The method of claim 9, which further comprises a step of administering a second anti-cancer agent.

11. The method of claim 10, wherein the second anti-cancer agent is erlotinib, afatinib, gefitinib, bevacizumab, ramucirumab, gefitinib, lapatinib, erlotinib, cisplatin, paclitaxel, methotrexate, cyclophosphamide, ifosfamide, chlorambucil, carmustine, carboplatin, vincristine, vinblastine, thiotepa, lomustine, semustine, 5-fluorouracil, corticosteroids, calcineurin inhibitors, NSAIDs, inhibitors of 5-lipoxygenase, or cytarabine.

12. The method of claim 10, which is a combined treatment or a maintenance treatment.

13. A peptide comprising an amino acid sequence consisting of the following:

FHAVELLA (LT-A3) (SEQ ID NO:10), FKAVELLA (LT-K2) (SEQ ID NO:11), FRAVELLA (LT-R2) (SEQ ID NO:12), FHAVDLLA (LT-D5) (SEQ ID NO:13), FHAVHLLA (LT-H5) (SEQ ID NO:14), FHAVOrnLLA (LT-Orn5) (SEQ ID NO:15), AHAVELLA (LT-A13) (SEQ ID NO:16), FHAAELLA (LT-A34) (SEQ ID NO:17), FHAVEALA (LT-A36) (SEQ ID NO:18), FHAAEALA (LT-A346) (SEQ ID NO:19), FAIVALLA (LT-A25) (SEQ ID NO:20), FEAVHLLA (LT-E2H5) (SEQ ID NO:21), WHAVELLA (LT-W1) (SEQ ID NO:23), FHAVELSA (LT-S7) (SEQ ID NO:24), FHAVELLS (LT-S8) (SEQ ID NO:25), DGNFHIVELLA (LT-11AA) (SEQ ID NO:26), FHIAELLA (LT-A4) (SEQ ID NO:29), FHIVALLA (LT-A5) (SEQ ID NO:30), FHIVEALA (LT-A6) (SEQ ID NO:31), or FHIVELAA (LT-A7) (SEQ ID NO:32); or a salt thereof.

14. A peptide comprising an amino acid sequence consisting of FHAVELLA (SEQ ID NO:10).

* * * * *

SEQUENCE LISTING

```
<160> NUMBER OF SEQ ID NOS: 32

<210> SEQ ID NO 1
<211> LENGTH: 91
<212> TYPE: PRT
<213> ORGANISM: artificial
<220> FEATURE:
<223> OTHER INFORMATION: synthetic polypeptide

<400> SEQUENCE: 1

Ala Ser Ala Ile Tyr Ser Val Glu Thr Ile Asn Asp Gly Asn Phe His
1               5                   10                  15

Ile Val Glu Leu Leu Ala Leu Asp Gln Ser Leu Ser Leu Ser Val Asp
            20                  25                  30

Gly Gly Asn Pro Lys Ile Ile Thr Asn Leu Ser Lys Gln Ser Thr Leu
        35                  40                  45
```

-continued

```
Asn Phe Asp Ser Pro Leu Tyr Val Gly Gly Met Pro Gly Lys Ser Asn
    50                  55                  60

Val Ala Ser Leu Arg Gln Ala Pro Gly Gln Asn Gly Thr Ser Phe His
65                  70                  75                  80

Gly Cys Ile Arg Asn Leu Tyr Ile Asn Ser Glu
                85                  90


<210> SEQ ID NO 2
<211> LENGTH: 22
<212> TYPE: PRT
<213> ORGANISM: artificial
<220> FEATURE:
<223> OTHER INFORMATION: synthetic peptide

<400> SEQUENCE: 2

Ala Ser Ala Ile Tyr Ser Val Glu Thr Ile Asn Asp Gly Asn Phe His
1               5                   10                  15

Ile Val Glu Leu Leu Ala
            20


<210> SEQ ID NO 3
<211> LENGTH: 26
<212> TYPE: PRT
<213> ORGANISM: artificial
<220> FEATURE:
<223> OTHER INFORMATION: synthetic peptide

<400> SEQUENCE: 3

Phe His Ile Val Glu Leu Leu Ala Leu Asp Gln Ser Leu Ser Leu Ser
1               5                   10                  15

Val Asp Gly Gly Asn Pro Lys Ile Ile Thr
            20                  25


<210> SEQ ID NO 4
<211> LENGTH: 22
<212> TYPE: PRT
<213> ORGANISM: artificial
<220> FEATURE:
<223> OTHER INFORMATION: synthetic peptide

<400> SEQUENCE: 4

Lys Ile Ile Thr Asn Leu Ser Lys Gln Ser Thr Leu Asn Phe Asp Ser
1               5                   10                  15

Pro Leu Tyr Val Gly Gly
            20


<210> SEQ ID NO 5
<211> LENGTH: 23
<212> TYPE: PRT
<213> ORGANISM: artificial
<220> FEATURE:
<223> OTHER INFORMATION: synthetic peptide

<400> SEQUENCE: 5

Gly Gly Met Pro Gly Lys Ser Asn Val Ala Ser Leu Arg Gln Ala Pro
1               5                   10                  15

Gly Gln Asn Gly Thr Ser Phe
            20


<210> SEQ ID NO 6
<211> LENGTH: 24
<212> TYPE: PRT
<213> ORGANISM: artificial
```

<220> FEATURE:
<223> OTHER INFORMATION: synthetic peptide

<400> SEQUENCE: 6

Leu Arg Gln Ala Pro Gly Gln Asn Gly Thr Ser Phe His Gly Cys Ile
1               5                   10                  15

Arg Asn Leu Tyr Ile Asn Ser Glu
            20

<210> SEQ ID NO 7
<211> LENGTH: 10
<212> TYPE: PRT
<213> ORGANISM: artificial
<220> FEATURE:
<223> OTHER INFORMATION: synthetic peptide

<400> SEQUENCE: 7

Ala Ser Ala Ile Tyr Ser Val Glu Thr Ile
1               5                   10

<210> SEQ ID NO 8
<211> LENGTH: 10
<212> TYPE: PRT
<213> ORGANISM: artificial
<220> FEATURE:
<223> OTHER INFORMATION: synthetic peptide

<400> SEQUENCE: 8

Glu Thr Ile Asn Asp Gly Asn Phe His Ile
1               5                   10

<210> SEQ ID NO 9
<211> LENGTH: 8
<212> TYPE: PRT
<213> ORGANISM: artificial
<220> FEATURE:
<223> OTHER INFORMATION: synthetic peptide

<400> SEQUENCE: 9

Phe His Ile Val Glu Leu Leu Ala
1               5

<210> SEQ ID NO 10
<211> LENGTH: 8
<212> TYPE: PRT
<213> ORGANISM: artificial
<220> FEATURE:
<223> OTHER INFORMATION: synthetic peptide

<400> SEQUENCE: 10

Phe His Ala Val Glu Leu Leu Ala
1               5

<210> SEQ ID NO 11
<211> LENGTH: 8
<212> TYPE: PRT
<213> ORGANISM: artificial
<220> FEATURE:
<223> OTHER INFORMATION: synthetic peptide

<400> SEQUENCE: 11

Phe Lys Ala Val Glu Leu Leu Ala
1               5

-continued

<210> SEQ ID NO 12
<211> LENGTH: 8
<212> TYPE: PRT
<213> ORGANISM: artificial
<220> FEATURE:
<223> OTHER INFORMATION: synthetic peptide

<400> SEQUENCE: 12

Phe Arg Ala Val Glu Leu Leu Ala
1               5

<210> SEQ ID NO 13
<211> LENGTH: 8
<212> TYPE: PRT
<213> ORGANISM: artificial
<220> FEATURE:
<223> OTHER INFORMATION: synthetic peptide

<400> SEQUENCE: 13

Phe His Ala Val Asp Leu Leu Ala
1               5

<210> SEQ ID NO 14
<211> LENGTH: 8
<212> TYPE: PRT
<213> ORGANISM: artificial
<220> FEATURE:
<223> OTHER INFORMATION: synthetic peptide

<400> SEQUENCE: 14

Phe His Ala Val His Leu Leu Ala
1               5

<210> SEQ ID NO 15
<211> LENGTH: 8
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa is Orn (Ornithine; O)

<400> SEQUENCE: 15

Phe His Ala Val Xaa Leu Leu Ala
1               5

<210> SEQ ID NO 16
<211> LENGTH: 8
<212> TYPE: PRT
<213> ORGANISM: artificial
<220> FEATURE:
<223> OTHER INFORMATION: synthetic peptide

<400> SEQUENCE: 16

Ala His Ala Val Glu Leu Leu Ala
1               5

<210> SEQ ID NO 17
<211> LENGTH: 8
<212> TYPE: PRT
<213> ORGANISM: artificial
<220> FEATURE:
<223> OTHER INFORMATION: synthetic peptide

<400> SEQUENCE: 17

Phe His Ala Ala Glu Leu Leu Ala
1 5

<210> SEQ ID NO 18
<211> LENGTH: 8
<212> TYPE: PRT
<213> ORGANISM: artificial
<220> FEATURE:
<223> OTHER INFORMATION: synthetic peptide

<400> SEQUENCE: 18

Phe His Ala Val Glu Ala Leu Ala
1 5

<210> SEQ ID NO 19
<211> LENGTH: 8
<212> TYPE: PRT
<213> ORGANISM: artificial
<220> FEATURE:
<223> OTHER INFORMATION: synthetic peptide

<400> SEQUENCE: 19

Phe His Ala Ala Glu Ala Leu Ala
1 5

<210> SEQ ID NO 20
<211> LENGTH: 8
<212> TYPE: PRT
<213> ORGANISM: artificial
<220> FEATURE:
<223> OTHER INFORMATION: synthetic peptide

<400> SEQUENCE: 20

Phe Ala Ile Val Ala Leu Leu Ala
1 5

<210> SEQ ID NO 21
<211> LENGTH: 8
<212> TYPE: PRT
<213> ORGANISM: artificial
<220> FEATURE:
<223> OTHER INFORMATION: synthetic peptide

<400> SEQUENCE: 21

Phe Glu Ala Val His Leu Leu Ala
1 5

<210> SEQ ID NO 22
<211> LENGTH: 8
<212> TYPE: PRT
<213> ORGANISM: artificial
<220> FEATURE:
<223> OTHER INFORMATION: synthetic peptide

<400> SEQUENCE: 22

Tyr His Ala Val Glu Leu Leu Ala
1 5

<210> SEQ ID NO 23
<211> LENGTH: 8
<212> TYPE: PRT
<213> ORGANISM: artificial
<220> FEATURE:
<223> OTHER INFORMATION: synthetic peptide

<400> SEQUENCE: 23

Trp His Ala Val Glu Leu Leu Ala
1 5

<210> SEQ ID NO 24
<211> LENGTH: 8
<212> TYPE: PRT
<213> ORGANISM: artificial
<220> FEATURE:
<223> OTHER INFORMATION: synthetic peptide

<400> SEQUENCE: 24

Phe His Ala Val Glu Leu Ser Ala
1 5

<210> SEQ ID NO 25
<211> LENGTH: 8
<212> TYPE: PRT
<213> ORGANISM: artificial
<220> FEATURE:
<223> OTHER INFORMATION: synthetic peptide

<400> SEQUENCE: 25

Phe His Ala Val Glu Leu Leu Ser
1 5

<210> SEQ ID NO 26
<211> LENGTH: 11
<212> TYPE: PRT
<213> ORGANISM: artificial
<220> FEATURE:
<223> OTHER INFORMATION: synthetic peptide

<400> SEQUENCE: 26

Asp Gly Asn Phe His Ile Val Glu Leu Leu Ala
1 5 10

<210> SEQ ID NO 27
<211> LENGTH: 8
<212> TYPE: PRT
<213> ORGANISM: artificial
<220> FEATURE:
<223> OTHER INFORMATION: synthetic peptide

<400> SEQUENCE: 27

Ala His Ile Val Glu Leu Leu Ala
1 5

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Phe Ala Ile Val Glu Leu Leu Ala
1 5

<210> SEQ ID NO 29
<211> LENGTH: 8
<212> TYPE: PRT
<213> ORGANISM: artificial
<220> FEATURE:
<223> OTHER INFORMATION: synthetic peptide -continued

```
<400> SEQUENCE: 29

Phe His Ile Ala Glu Leu Leu Ala
1               5


<210> SEQ ID NO 30
<211> LENGTH: 8
<212> TYPE: PRT
<213> ORGANISM: artificial
<220> FEATURE:
<223> OTHER INFORMATION: synthetic peptide

<400> SEQUENCE: 30

Phe His Ile Val Ala Leu Leu Ala
1               5


<210> SEQ ID NO 31
<211> LENGTH: 8
<212> TYPE: PRT
<213> ORGANISM: artificial
<220> FEATURE:
<223> OTHER INFORMATION: synthetic peptide

<400> SEQUENCE: 31

Phe His Ile Val Glu Ala Leu Ala
1               5


<210> SEQ ID NO 32
<211> LENGTH: 8
<212> TYPE: PRT
<213> ORGANISM: artificial
<220> FEATURE:
<223> OTHER INFORMATION: synthetic peptide

<400> SEQUENCE: 32

Phe His Ile Val Glu Leu Ala Ala
1               5
```